(12) United States Patent
Sengun

(10) Patent No.: US 10,524,777 B2
(45) Date of Patent: *Jan. 7, 2020

(54) SYSTEMS, DEVICES, AND METHODS FOR SECURING TISSUE

(71) Applicant: Medos International Sàrl, Le Locle (CH)

(72) Inventor: Mehmet Ziya Sengun, Canton, MA (US)

(73) Assignee: MEDOS INTERNATIONAL SÀRL, Le Locle (CH)

( * ) Notice: Subject to any disclaimer, the term of this patent is extended or adjusted under 35 U.S.C. 154(b) by 157 days.

This patent is subject to a terminal disclaimer.

(21) Appl. No.: 15/700,901

(22) Filed: Sep. 11, 2017

(65) Prior Publication Data

US 2017/0367690 A1 Dec. 28, 2017

Related U.S. Application Data

(60) Continuation of application No. 14/713,566, filed on May 15, 2015, now Pat. No. 9,757,116, which is a
(Continued)

(51) Int. Cl.
*A61B 17/04* (2006.01)
*A61B 17/06* (2006.01)
*A61B 17/12* (2006.01)

(52) U.S. Cl.
CPC .... *A61B 17/0401* (2013.01); *A61B 17/06166* (2013.01); *A61B 17/0485* (2013.01);
(Continued)

(58) Field of Classification Search
CPC .......... A61B 17/0401; A61B 17/06166; A61B 17/0485; A61B 17/12009; A61B 2017/0475; A61B 2017/0477
See application file for complete search history.

(56) References Cited

U.S. PATENT DOCUMENTS 2,566,625 A 9/1951 Nagelmann
2,600,395 A 6/1952 Domoj et al.
(Continued)

FOREIGN PATENT DOCUMENTS

AU 2008229746 A1 10/2008
CA 2772500 A1 9/2013
(Continued)

OTHER PUBLICATIONS

**[NA8:A41O Author Listed] Arthroscopic Knot Tying Manual 2005. DePuy Mitek. 27 pages.
(Continued)

*Primary Examiner* — Todd J Scherbel

(57) ABSTRACT

Systems, devices, and methods are provided for securing soft tissue to bone, for securing one or more objects using a surgical filament, and for drawing two or more tissues together so they can be secured in a desired location. One exemplary embodiment of a surgical repair construct that is configured to atraumatically pass through soft tissue to secure tissue in a knotless manner includes a snare linkage, a collapsible loop, and a flexible suture pin. The snare linkage can include a collapsible snare for receiving the collapsible loop, and in use the snare can be collapsed around the collapsible loop and advanced distally towards the bone until the snare is proximate to the tissue, while the collapsible loop can be collapsed distally towards the bone to bring the tissue into proximity with the bone. Other exemplary systems, devices, and methods for use with soft tissue repair are also provided.

25 Claims, 12 Drawing Sheets

Related U.S. Application Data division of application No. 13/465,288, filed on May 7, 2012, now Pat. No. 9,060,763.

(52) U.S. Cl.
CPC ... *A61B 17/12009* (2013.01); *A61B 17/12013* (2013.01); *A61B 2017/0414* (2013.01); *A61B 2017/0427* (2013.01); *A61B 2017/0458* (2013.01); *A61B 2017/0475* (2013.01); *A61B 2017/0477* (2013.01); *A61B 2017/06185* (2013.01)

(56) References Cited

U.S. PATENT DOCUMENTS

| | | |
|---|---|---|
| 2,697,624 A | 12/1954 | Thomas et al. |
| 2,758,858 A | 8/1956 | Smith |
| 2,992,029 A | 7/1961 | Russell |
| 3,106,417 A | 10/1963 | Clow |
| 3,131,957 A | 5/1964 | Musto |
| 3,177,021 A | 4/1965 | Benham |
| 3,402,957 A | 9/1968 | Peterson |
| 3,521,918 A | 7/1970 | Hammond |
| 3,565,077 A | 2/1971 | Glick |
| 3,580,256 A | 5/1971 | Wilkinson et al. |
| 3,712,651 A | 1/1973 | Shockley |
| 3,752,516 A | 8/1973 | Mumma |
| 3,873,140 A | 3/1975 | Bloch |
| 4,029,346 A | 6/1977 | Browning |
| 4,036,101 A | 7/1977 | Burnett |
| 4,038,988 A | 8/1977 | Perisse |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,186,921 A | 2/1980 | Fox |
| 4,205,399 A | 6/1980 | Shalaby et al. |
| 4,208,511 A | 6/1980 | Shalaby et al. |
| 4,319,428 A | 3/1982 | Fox |
| 4,403,797 A | 9/1983 | Ragland, Jr. |
| 4,510,934 A | 4/1985 | Batra |
| 4,572,554 A | 2/1986 | Janssen et al. |
| 4,792,336 A | 12/1988 | Hlavacek et al. |
| 4,870,957 A | 10/1989 | Goble et al. |
| 4,946,377 A | 8/1990 | Kovach |
| 4,962,929 A | 10/1990 | Melton, Jr. |
| 4,987,665 A | 1/1991 | Dumican et al. |
| 5,062,344 A | 11/1991 | Gerker |
| 5,098,137 A | 3/1992 | Wardall |
| 5,144,961 A | 9/1992 | Chen et al. |
| 5,156,616 A | 10/1992 | Meadows et al. |
| 5,178,629 A | 1/1993 | Kammerer |
| 5,217,495 A | 6/1993 | Kaplan et al. |
| 5,250,053 A | 10/1993 | Snyder |
| 5,250,054 A | 10/1993 | Li |
| 5,259,846 A | 11/1993 | Granger et al. |
| 5,263,984 A | 11/1993 | Li et al. |
| 5,279,311 A | 1/1994 | Snyder |
| 5,282,809 A | 2/1994 | Kammerer et al. |
| 5,284,485 A | 2/1994 | Kammerer et al. |
| 5,312,423 A | 5/1994 | Rosenbluth et al. |
| 5,318,575 A | 6/1994 | Chesterfield et al. |
| 5,320,629 A | 6/1994 | Noda et al. |
| 5,376,118 A | 12/1994 | Kaplan et al. |
| 5,391,176 A | 2/1995 | de la Torre |
| 5,395,382 A | 3/1995 | DiGiovanni et al. |
| 5,405,352 A | 4/1995 | Weston |
| 5,450,860 A | 9/1995 | O'Connor |
| 5,454,820 A | 10/1995 | Kammerer et al. |
| 5,456,722 A | 10/1995 | McLeod et al. |
| 5,464,427 A | 11/1995 | Curtis et al. |
| 5,464,929 A | 11/1995 | Bezwada et al. |
| 5,472,446 A | 12/1995 | de la Torre |
| 5,527,323 A | 6/1996 | Jervis et al. |
| 5,534,011 A | 7/1996 | Greene, Jr. et al. |
| 5,540,703 A | 7/1996 | Barker, Jr. et al. |
| 5,549,618 A | 8/1996 | Fleenor et al. |
| 5,562,684 A | 10/1996 | Kammerer |
| 5,569,306 A | 10/1996 | Thal |
| 5,571,139 A | 11/1996 | Jenkins, Jr. |
| 5,573,286 A | 11/1996 | Rogozinski |
| 5,591,207 A | 1/1997 | Coleman |
| 5,593,189 A | 1/1997 | Little |
| 5,595,751 A | 1/1997 | Bezwada et al. |
| 5,597,579 A | 1/1997 | Bezwada et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,628,756 A | 5/1997 | Barker |
| 5,645,850 A | 7/1997 | Bezwada et al. |
| 5,647,616 A | 7/1997 | Hamilton |
| 5,647,874 A | 7/1997 | Hayhurst |
| 5,648,088 A | 7/1997 | Bezwada et al. |
| 5,667,528 A | 9/1997 | Colligan |
| 5,683,417 A | 11/1997 | Cooper |
| 5,683,419 A | 11/1997 | Thal |
| 5,685,037 A | 11/1997 | Fitzner et al. |
| 5,698,213 A | 12/1997 | Jamiolkowski et al. |
| 5,700,583 A | 12/1997 | Jamiolkowski et al. |
| 5,702,397 A | 12/1997 | Goble et al. |
| 5,709,708 A | 1/1998 | Thal |
| 5,716,368 A | 2/1998 | de la Torre et al. |
| 5,725,556 A | 3/1998 | Moser et al. |
| 5,728,109 A | 3/1998 | Schulze et al. |
| 5,741,332 A | 4/1998 | Schmitt |
| 5,749,898 A | 5/1998 | Schulze et al. |
| 5,782,864 A | 7/1998 | Lizardi |
| 5,814,069 A | 9/1998 | Schulze et al. |
| 5,859,150 A | 1/1999 | Jamiolkowski et al. |
| 5,899,920 A | 5/1999 | DeSatnick et al. |
| 5,941,900 A | 8/1999 | Bonutti |
| 5,964,783 A | 10/1999 | Grafton et al. |
| 5,971,447 A | 10/1999 | Steck, III |
| 5,989,252 A | 11/1999 | Fumex |
| 6,024,758 A | 2/2000 | Thal |
| 6,045,574 A | 4/2000 | Thal |
| 6,143,017 A | 11/2000 | Thal |
| 6,221,084 B1 | 4/2001 | Fleenor |
| 6,267,766 B1 | 7/2001 | Burkhart |
| 6,296,659 B1 | 10/2001 | Foerster |
| 6,319,271 B1 | 11/2001 | Schwartz et al. |
| 6,322,112 B1 | 11/2001 | Duncan |
| 6,517,578 B2 | 2/2003 | Hein |
| 6,527,794 B1 | 3/2003 | McDevitt et al. |
| 6,527,795 B1 | 3/2003 | Lizardi |
| 6,540,750 B2 | 4/2003 | Burkhart |
| 6,547,807 B2 | 4/2003 | Chan et al. |
| 6,596,015 B1 | 7/2003 | Pitt et al. |
| 6,641,596 B1 | 11/2003 | Lizardi |
| 6,641,597 B2 | 11/2003 | Burkhart et al. |
| 6,652,563 B2 | 11/2003 | Dreyfuss |
| 6,660,023 B2 | 12/2003 | McDevitt et al. |
| 6,689,154 B2 | 2/2004 | Bartlett |
| 6,716,234 B2 | 4/2004 | Grafton et al. |
| 6,767,037 B2 | 7/2004 | Wenstrom, Jr. |
| 6,818,010 B2 | 11/2004 | Eichhorn et al. |
| 6,887,259 B2 | 5/2005 | Lizardi |
| 6,923,824 B2 | 8/2005 | Morgan et al. |
| 6,994,719 B2 | 2/2006 | Grafton |
| 7,029,490 B2 | 4/2006 | Grafton et al. |
| 7,048,754 B2 | 5/2006 | Martin et al. |
| 7,081,126 B2 | 7/2006 | McDevitt et al. |
| 7,217,279 B2 | 5/2007 | Reese |
| 7,226,469 B2 | 6/2007 | Benavitz et al. |
| 7,235,090 B2 | 6/2007 | Buckman et al. |
| 7,285,124 B2 | 10/2007 | Foerster |
| 7,309,337 B2 | 12/2007 | Colleran et al. |
| 7,338,502 B2 | 3/2008 | Rosenblatt |
| 7,381,213 B2 | 6/2008 | Lizardi |
| 7,390,332 B2 | 6/2008 | Selvitelli et al. |
| 7,455,684 B2 | 11/2008 | Gradel et al. |
| 7,582,105 B2 | 9/2009 | Kolster |
| 7,601,165 B2 | 10/2009 | Stone |
| 7,651,509 B2 | 1/2010 | Bojarski et al. |

(56) References Cited

U.S. PATENT DOCUMENTS

| | | |
|---|---|---|
| 7,654,321 B2 | 2/2010 | Zazovsky et al. |
| 7,658,750 B2 | 2/2010 | Li |
| 7,658,751 B2 | 2/2010 | Stone et al. |
| 7,682,374 B2 | 3/2010 | Foerster et al. |
| 7,695,495 B2 | 4/2010 | Dreyfuss |
| 7,703,372 B1 | 4/2010 | Shakespeare |
| 7,803,173 B2 | 9/2010 | Burkhart et al. |
| 7,875,043 B1 | 1/2011 | Ashby et al. |
| 7,883,528 B2 | 2/2011 | Grafton et al. |
| 7,883,529 B2 | 2/2011 | Sinnott et al. |
| 7,905,903 B2 | 3/2011 | Stone et al. |
| 7,905,904 B2 | 3/2011 | Stone et al. |
| 7,959,650 B2 | 6/2011 | Kaiser |
| 7,981,140 B2 | 7/2011 | Burkhart |
| 8,012,171 B2 | 9/2011 | Schmieding |
| 8,088,130 B2 | 1/2012 | Kaiser et al. |
| 8,088,146 B2 | 1/2012 | Wert et al. |
| 8,114,128 B2 | 2/2012 | Cauldwell et al. |
| 8,118,836 B2 | 2/2012 | Denham et al. |
| 8,137,382 B2 | 3/2012 | Denham et al. |
| 8,231,653 B2 | 7/2012 | Dreyfuss |
| 8,231,654 B2 | 7/2012 | Kaiser et al. |
| 8,419,769 B2 | 4/2013 | Thal |
| 8,545,535 B2 | 10/2013 | Hirotsuka et al. |
| 8,608,758 B2 | 12/2013 | Singhatat et al. |
| 8,790,369 B2 | 7/2014 | Orphanos et al. |
| 8,790,370 B2 | 7/2014 | Spenciner et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 8,894,684 B2 | 11/2014 | Sengun |
| 8,974,495 B2 | 3/2015 | Hernandez et al. |
| 9,017,381 B2 | 4/2015 | Kaiser et al. |
| 9,034,013 B2 | 5/2015 | Sengun |
| 9,060,763 B2 * | 6/2015 | Sengun .............. A61B 17/0401 |
| 9,060,764 B2 | 6/2015 | Sengun |
| 9,095,331 B2 | 8/2015 | Hernandez et al. |
| 9,179,908 B2 | 11/2015 | Sengun |
| 9,192,373 B2 | 11/2015 | Sengun |
| 9,198,653 B2 | 12/2015 | Sengun et al. |
| 9,271,716 B2 | 3/2016 | Sengun |
| 9,345,468 B2 | 5/2016 | Sengun et al. |
| 9,345,567 B2 | 5/2016 | Sengun |
| 9,532,778 B2 | 1/2017 | Sengun et al. |
| 9,737,293 B2 | 8/2017 | Sengun et al. |
| 9,757,116 B2 * | 9/2017 | Sengun .............. A61B 17/0401 |
| 9,763,655 B2 | 9/2017 | Sengun |
| 9,795,373 B2 | 10/2017 | Sengun |
| 9,833,229 B2 | 12/2017 | Hernandez et al. |
| 9,872,678 B2 | 1/2018 | Spenciner et al. |
| 2002/0019649 A1 | 2/2002 | Sikora et al. |
| 2002/0029066 A1 | 3/2002 | Foerster |
| 2003/0004545 A1 | 1/2003 | Burkhart et al. |
| 2003/0050667 A1 | 3/2003 | Grafton et al. |
| 2003/0120309 A1 | 6/2003 | Colleran et al. |
| 2003/0130695 A1 | 7/2003 | McDevitt et al. |
| 2003/0229362 A1 | 12/2003 | Chan et al. |
| 2004/0093031 A1 | 5/2004 | Burkhart et al. |
| 2004/0098050 A1 | 5/2004 | Foerster et al. |
| 2004/0153074 A1 | 8/2004 | Bojarski et al. |
| 2004/0172062 A1 | 9/2004 | Burkhart |
| 2004/0236373 A1 | 11/2004 | Anspach |
| 2005/0033363 A1 | 2/2005 | Bojarski et al. |
| 2005/0119696 A1 | 6/2005 | Walters et al. |
| 2005/0137624 A1 | 6/2005 | Fallman |
| 2005/0187577 A1 | 8/2005 | Selvitelli et al. |
| 2005/0251208 A1 | 11/2005 | Elmer et al. |
| 2006/0106423 A1 | 5/2006 | Weisel et al. |
| 2006/0178680 A1 | 8/2006 | Nelson et al. |
| 2006/0178702 A1 | 8/2006 | Pierce et al. |
| 2006/0293710 A1 | 12/2006 | Foerster et al. |
| 2007/0027476 A1 | 2/2007 | Harris et al. |
| 2007/0032792 A1 | 2/2007 | Collin et al. |
| 2007/0060922 A1 | 3/2007 | Dreyfuss |
| 2007/0083236 A1 | 4/2007 | Sikora et al. |
| 2007/0135843 A1 | 6/2007 | Burkhart |
| 2007/0150003 A1 | 6/2007 | Dreyfuss et al. |
| 2007/0156148 A1 | 7/2007 | Fanton et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0219557 A1 | 9/2007 | Bourque et al. |
| 2007/0219558 A1 | 9/2007 | Deutsch |
| 2007/0225719 A1 | 9/2007 | Stone et al. |
| 2007/0239209 A1 | 10/2007 | Fallman |
| 2008/0009901 A1 | 1/2008 | Redmond et al. |
| 2008/0009904 A1 | 1/2008 | Bourque et al. |
| 2008/0027446 A1 | 1/2008 | Stone et al. |
| 2008/0065114 A1 | 3/2008 | Stone et al. |
| 2008/0077182 A1 | 3/2008 | Geissler et al. |
| 2008/0091237 A1 | 4/2008 | Schwartz et al. |
| 2008/0103528 A1 | 5/2008 | Zirps et al. |
| 2008/0140092 A1 | 6/2008 | Stone et al. |
| 2008/0147063 A1 | 6/2008 | Cauldwell et al. |
| 2008/0188893 A1 | 8/2008 | Selvitelli et al. |
| 2008/0195205 A1 | 8/2008 | Schwartz |
| 2008/0208265 A1 | 8/2008 | Frazier et al. |
| 2008/0228265 A1 | 9/2008 | Spence et al. |
| 2008/0255613 A1 | 10/2008 | Kaiser et al. |
| 2008/0275469 A1 | 11/2008 | Fanton et al. |
| 2008/0312689 A1 | 12/2008 | Denham et al. |
| 2009/0023984 A1 | 1/2009 | Stokes et al. |
| 2009/0036905 A1 | 2/2009 | Schmieding |
| 2009/0043317 A1 | 2/2009 | Cavanaugh et al. |
| 2009/0054928 A1 | 2/2009 | Denham et al. |
| 2009/0062850 A1 | 3/2009 | Ken |
| 2009/0062854 A1 | 3/2009 | Kaiser et al. |
| 2009/0082805 A1 | 3/2009 | Kaiser et al. |
| 2009/0082807 A1 | 3/2009 | Miller et al. |
| 2009/0088798 A1 | 4/2009 | Snyder et al. |
| 2009/0099598 A1 | 4/2009 | McDevitt et al. |
| 2009/0138042 A1 | 5/2009 | Thal |
| 2009/0234387 A1 | 9/2009 | Miller et al. |
| 2009/0281568 A1 | 11/2009 | Cendan et al. |
| 2009/0281581 A1 | 11/2009 | Berg |
| 2009/0287246 A1 | 11/2009 | Cauldwell et al. |
| 2009/0306711 A1 | 12/2009 | Stone et al. |
| 2009/0312776 A1 | 12/2009 | Kaiser et al. |
| 2009/0312794 A1 | 12/2009 | Nason et al. |
| 2009/0318958 A1 | 12/2009 | Ochiai |
| 2010/0004683 A1 | 1/2010 | Hoof et al. |
| 2010/0016892 A1 | 1/2010 | Kaiser et al. |
| 2010/0094425 A1 | 4/2010 | Bentley et al. |
| 2010/0162882 A1 | 7/2010 | Shakespeare |
| 2010/0204730 A1 | 8/2010 | Maiorino et al. |
| 2010/0249809 A1 | 9/2010 | Singhatat et al. |
| 2010/0249834 A1 | 9/2010 | Dreyfuss |
| 2010/0256677 A1 | 10/2010 | Albertorio et al. |
| 2010/0292732 A1 | 11/2010 | Hirotsuka et al. |
| 2010/0292792 A1 | 11/2010 | Stone et al. |
| 2011/0022083 A1 | 1/2011 | DiMatteo et al. |
| 2011/0022084 A1 | 1/2011 | Sengun et al. |
| 2011/0077667 A1 | 3/2011 | Singhatat et al. |
| 2011/0098727 A1 | 4/2011 | Kaiser et al. |
| 2011/0152928 A1 | 6/2011 | Colleran et al. |
| 2011/0190815 A1 | 8/2011 | Saliman |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0238111 A1 | 9/2011 | Frank |
| 2011/0264140 A1 | 10/2011 | Lizardi et al. |
| 2011/0264141 A1 | 10/2011 | Denham et al. |
| 2011/0270278 A1 | 11/2011 | Overes et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0101523 A1 | 4/2012 | Wert et al. |
| 2012/0101524 A1 | 4/2012 | Bennett |
| 2012/0130423 A1 | 5/2012 | Sengun et al. |
| 2012/0130424 A1 | 5/2012 | Sengun et al. |
| 2012/0150223 A1 | 6/2012 | Manos et al. |
| 2012/0165864 A1 | 6/2012 | Hernandez et al. |
| 2012/0179199 A1 | 7/2012 | Hernandez et al. |

(56) References Cited

U.S. PATENT DOCUMENTS

| | | |
|---|---|---|
| 2012/0253389 A1 | 10/2012 | Sengun et al. |
| 2012/0253390 A1 | 10/2012 | Sengun |
| 2012/0296375 A1 | 11/2012 | Thal |
| 2013/0110165 A1 | 5/2013 | Burkhart et al. |
| 2013/0158598 A1 | 6/2013 | Lizardi |
| 2013/0261664 A1 | 10/2013 | Spenciner et al. |
| 2013/0296895 A1 | 11/2013 | Sengun |
| 2013/0296896 A1 | 11/2013 | Sengun |
| 2013/0296931 A1 | 11/2013 | Sengun |
| 2013/0296934 A1 | 11/2013 | Sengun |
| 2014/0081324 A1 | 3/2014 | Sengun |
| 2014/0107701 A1 | 4/2014 | Lizardi et al. |
| 2014/0188163 A1 | 7/2014 | Sengun |
| 2014/0188164 A1 | 7/2014 | Sengun |
| 2014/0277132 A1 | 9/2014 | Sengun et al. |
| 2014/0330312 A1 | 11/2014 | Spenciner et al. |
| 2014/0343606 A1 | 11/2014 | Hernandez et al. |
| 2014/0343607 A1 | 11/2014 | Sengun et al. |
| 2015/0012038 A1 | 1/2015 | Sengun et al. |
| 2015/0025572 A1 | 1/2015 | Sengun |
| 2015/0045832 A1 | 2/2015 | Sengun |
| 2015/0238183 A1 | 8/2015 | Sengun |
| 2015/0245832 A1 | 9/2015 | Sengun |
| 2015/0297214 A1 | 10/2015 | Hernandez et al. |
| 2015/0313587 A1 | 11/2015 | Lizardi et al. |
| 2016/0128687 A1 | 5/2016 | Sengun |
| 2016/0278761 A1 | 9/2016 | Sengun et al. |
| 2016/0296222 A1 | 10/2016 | Sengun |
| 2017/0000479 A1 | 1/2017 | Sengun et al. |
| 2017/0303913 A1 | 10/2017 | Sengun et al. |
| 2017/0360428 A1 | 12/2017 | Sengun |

FOREIGN PATENT DOCUMENTS

| | | |
|---|---|---|
| CN | 2719234 Y | 8/2005 |
| CN | 101252887 A | 8/2008 |
| CN | 101442944 A | 5/2009 |
| CN | 101961256 A | 2/2011 |
| CN | 102113901 A | 7/2011 |
| EP | 0 870 471 A1 | 10/1998 |
| EP | 1 199 035 A1 | 4/2002 |
| EP | 1 707 127 A1 | 10/2006 |
| EP | 2 277 457 A1 | 1/2011 |
| EP | 2 455 003 A2 | 5/2012 |
| EP | 2 572 650 A1 | 3/2013 |
| JP | 2000-512193 A | 9/2000 |
| JP | 2008-543509 A | 12/2008 |
| WO | 95/019139 A1 | 7/1995 |
| WO | 97/017901 A1 | 5/1997 |
| WO | 98/011825 A1 | 3/1998 |
| WO | 98/042261 A1 | 10/1998 |
| WO | 01/06933 A2 | 2/2001 |
| WO | 03/022161 A1 | 3/2003 |
| WO | 2007/002561 A1 | 1/2007 |
| WO | 2007/005394 A1 | 1/2007 |
| WO | 2007/078281 A2 | 7/2007 |
| WO | 2007/109769 A1 | 9/2007 |

OTHER PUBLICATIONS

\*\*[No Author Listed] Gryphon Brochure. DePuy Mitek. 2 pages (undated).
\*\*[No Author Listed] Versalok Anchor. Brochure. DePuy Mitek, a Johnson & Johnson company, 92 pages, 2007.
\*\*Allcock, The Encyclopedia of Polymer Science, vol. 13, pp. 31-41, Wiley Intersciences, John Wiley & Sons, 1988.
\*\*Chinese Office Action for Application No. 201310163420.7, dated May 5, 2016 (21 pages).
\*\*Chinese Office Action for Application No. 201310163700.8 dated Jun. 3, 2016 (14 pages).
\*\*Chinese Office Action for Application No. 201310429109.2 dated Oct. 24, 2016 (13 pages).
\*\*Chinese Office Action for Application No. 201310741440.8, dated Jan. 26, 2017 (12 pages).
\*\*Cohn et al., Biodegradable PEO/PLA block copolymers. J Biomed Mater Res. Nov. 1988;22(11):993-1009.
\*\*Cohn et al., Polym Preprint. 1989;30(1):498.
\*\*Dahl et al., Biomechanical characteristics of 9 arthroscopic knots. Arthroscopy. Jun. 2010;26(6):813-8.
\*\*EP Search Report for Application No. 11190157.5 dated Feb. 27, 2012. (8 pages).
\*\*Extended European Search Report for Application No. 11190157.5 dated Jul. 6, 2012. (10 pages).
\*\*EP Search Report for Application No. 11190159.1 dated Feb. 21, 2012. (8 pages).
\*\*Extended European Search Report for Application No. 11190159.1 dated Jul. 6, 2012. (11 pages).
\*\*Extended European Search Report for Application No. 11195100.0 dated Oct. 17, 2012. (7 pages).
\*\*Extended European Search Report for Application No. 13166905.3 dated Aug. 13, 2013 (9 Pages).
\*\*Extended European Search Report for Application No. 13166907.9, dated Aug. 1, 2013 (6 pages).
\*\*Extended European Search Report for Application No. 13166908.7, dated Aug. 23, 2013 (8 pages).
\*\*Extended European Search Report for Application No. 13185425.9 dated Dec. 16, 2013 (9 Pages).
\*\*Extended European Search Report for Application No. 13199724.9 dated Apr. 4, 2014 (6 Pages).
\*\*Extended European Search Report for Application No. 16205548.7, dated Dec. 22, 2017 (11 pages).
\*\*Heller, Handbook of Biodegradable Polymers, edited by Domb, et al., Hardwood Academic Press, pp. 99-118 (1997).
\*\*International Search Report for Application No. PCT/US2011/067119, dated Jun. 4, 2012. (6 pages).
\*\*Japanese Office Action for Application No. 2011-281088, dated Nov. 10, 2015 (4 pages).
\*\*Japanese Office Action for Application No. 2013-097645, dated May 9, 2017 (6 pages).
\*\*Japanese Office Action for Application No. 2013-268840, dated Sep. 26, 2017 (5 pages).
\*\*Kemnitzer et al., Handbook of biodegradable Polymers. Eds. Domb et al. Hardwood Acad. Press. 1997;251-72.
\*\*Vandorpe et al., Handbook of Biodegradable Polymers, edited by Domb, et al., Hardwood Acad. Press, pp. 161-182 (1997).
U.S. Appl. No. 12/977,146, filed Dec. 23, 2010, Adjustable Anchor Systems and Methods.
U.S. Appl. No. 12/977,154, filed Dec. 23, 2010, Surgical Filament Snare Assemblies.
U.S. Appl. No. 13/218,810, filed Aug. 26, 2011, Surgical Filament Snare Assemblies.
U.S. Appl. No. 13/336,151, filed Dec. 23, 2011, Adjustable Anchor Systems and Methods.
U.S. Appl. No. 13/435,790, filed Mar. 30, 2012, Surgical Filament Assemblies.
U.S. Appl. No. 13/435,834, filed Mar. 30, 2012, Surgical Filament Snare Assemblies.
U.S. Appl. No. 13/435,846, filed Mar. 30, 2012, Surgical Filament Snare Assemblies.
U.S. Appl. No. 13/465,288, filed May 7, 2012, Systems, Devices, and Methods for Securing Tissue.
U.S. Appl. No. 13/465,299, filed May 7, 2012, Systems, Devices, and Methods for Securing Tissue.
U.S. Appl. No. 13/465,362, filed May 7, 2012, Systems, Devices, and Methods for Securing Tissue Using a Suture Having One or More Protrusions.
U.S. Appl. No. 13/465,376, filed May 7, 2012, Systems, Devices, and Methods for Securing Tissue Using Snare Assemblies and Soft Anchors.
U.S. Appl. No. 13/623,429, filed Sep. 20, 2012, Systems, Devices, and Methods for Securing Tissue Using Hard Anchors.
U.S. Appl. No. 13/728,044, filed Dec. 27, 2012, Surgical Constructs and Methods for Securing Tissue.
U.S. Appl. No. 14/145,486, filed Dec. 31, 2013, Surgical Constructs With Collapsing Suture Loop and Methods for Securing Tissue.

(56) References Cited

OTHER PUBLICATIONS

U.S. Appl. No. 14/145,501, filed Dec. 31, 2013, Surgical Constructs and Methods for Securing Tissue.
U.S. Appl. No. 14/334,844, filed Jul. 18, 2014, Surgical Filament Assemblies.
U.S. Appl. No. 14/448,812, filed Jul. 31, 2014, Adjustable Anchor Systems and Methods.
U.S. Appl. No. 14/448,827, filed Jul. 31, 2014, Surgical Filament Snare Assemblies.
U.S. Appl. No. 14/448,847, filed Jul. 31, 2014, Surgical Filament Snare Assemblies.
U.S. Appl. No. 14/522,562, filed Oct. 23, 2014, Systems, Devices, and Methods for Securing Tissue Using a Suture Having One or More Protrusions.
U.S. Appl. No. 14/711,959, filed May 14, 2015, Systems, Devices, and Methods for Securing Tissue Using a Suture Having One or More Protrusions.
U.S. Appl. No. 14/713,566, filed May 15, 2015, Systems, Devices, and Methods for Securing Tissue.
U.S. Appl. No. 14/754,773, filed Jun. 30, 2015, Adjustable Anchor Systems and Methods.
U.S. Appl. No. 15/001,513, filed Jan. 20, 2016 Surgical Constructs and Methods for Securing Tissue.
U.S. Appl. No. 15/143,496, filed Apr. 29, 2016, Systems, Devices, and Methods for Securing Tissue Using Snare Assemblies and Soft Anchors.
U.S. Appl. No. 15/143,502, filed Apr. 29, 2016, Surgical Filament Snare Assemblies.
U.S. Appl. No. 15/264,645, filed Sep. 14, 2016, Surgical Filament Snare Assemblies.
U.S. Appl. No. 15/648,068, filed Jul. 12, 2017, Surgical Constructs With Collapsing Suture Loop and Methods for Securing Tissue.
U.S. Appl. No. 15/692,885, filed Aug. 31, 2017, Systems, Devices, and Methods for Securing Tissue Using Hard Anchors.
U.S. Appl. No. 15/794,625, filed Oct. 26, 2017, Adjustable Anchor Systems and Methods.

* cited by examiner

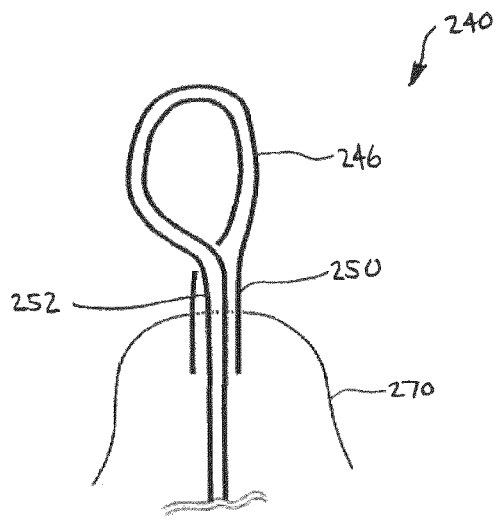
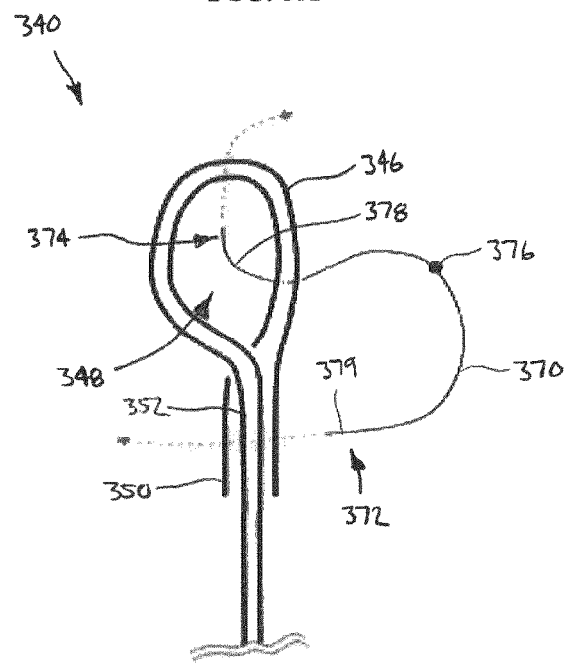
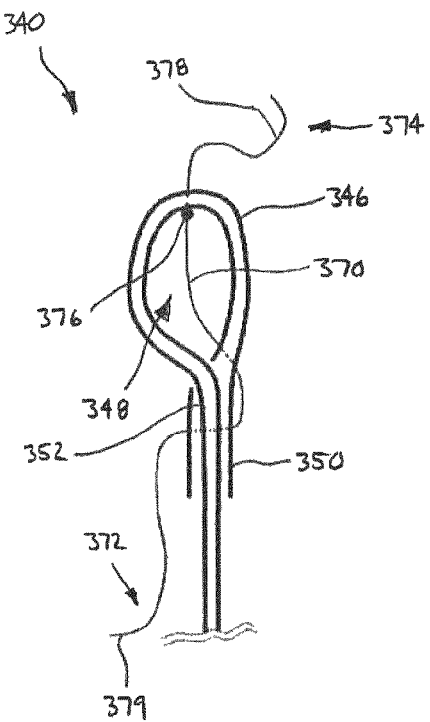

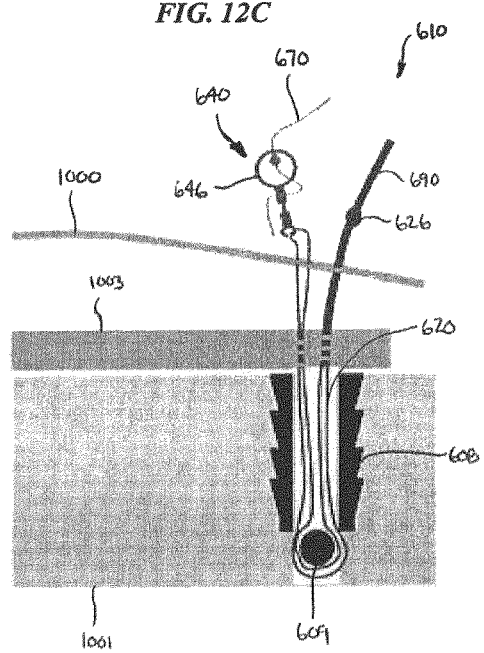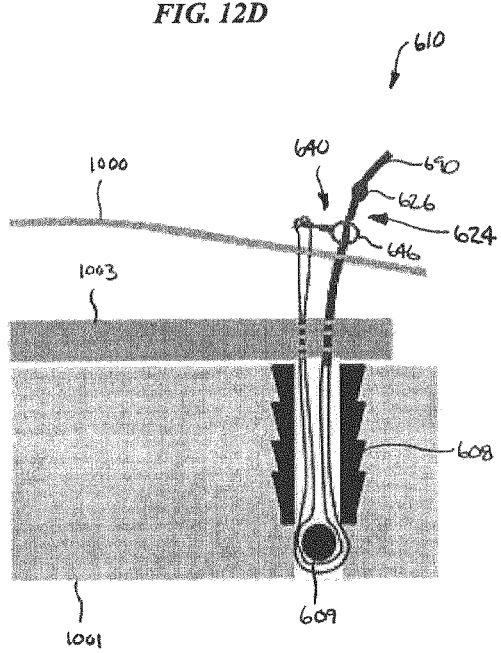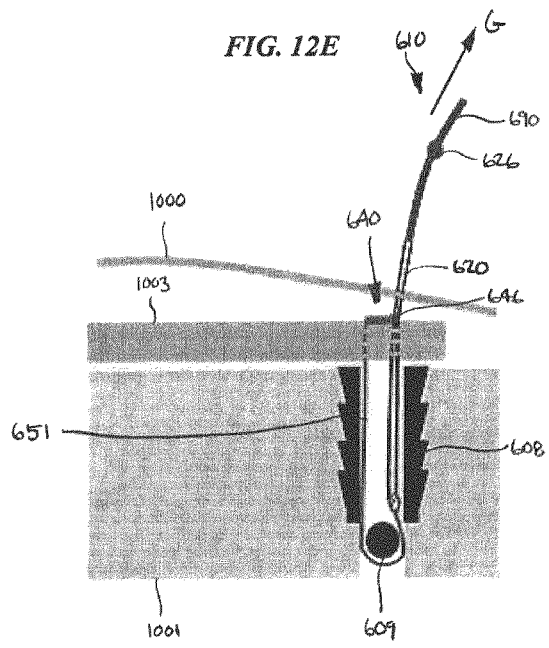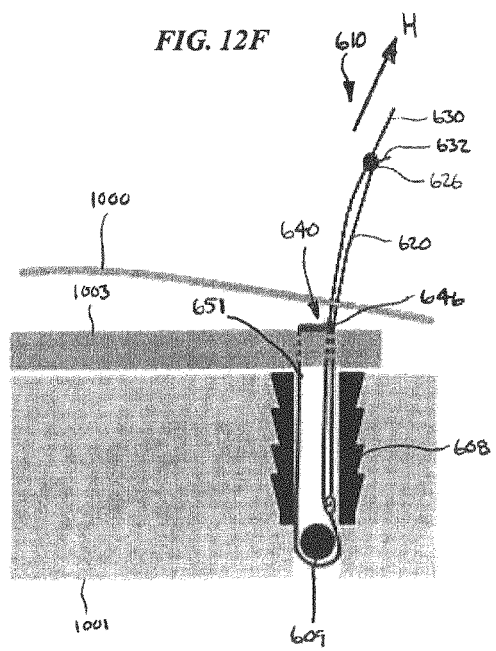

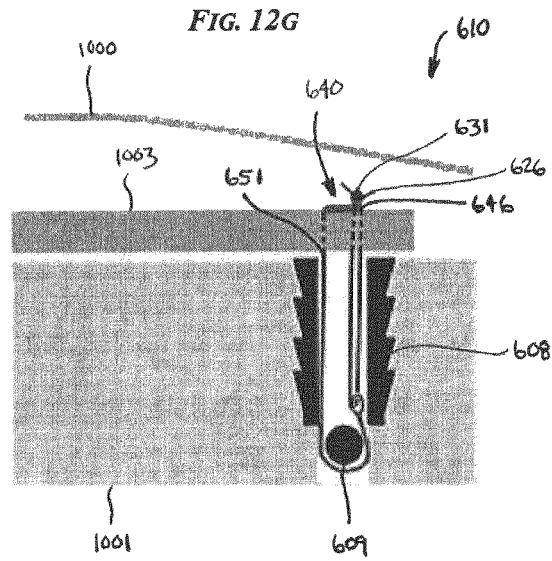
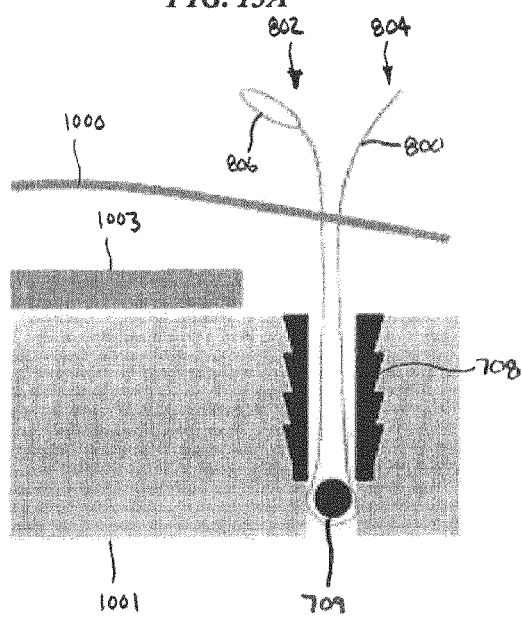
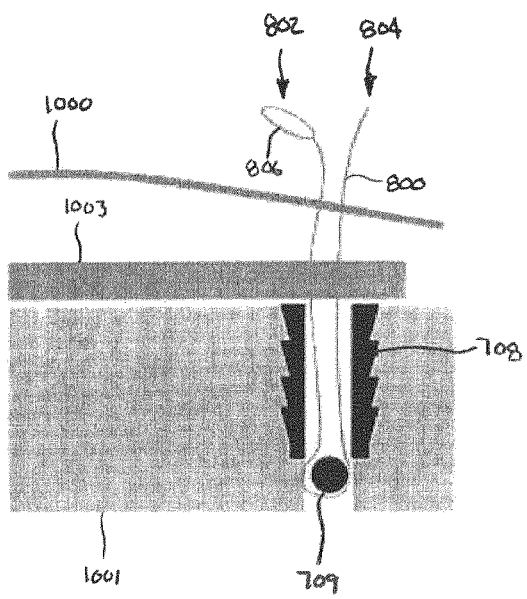

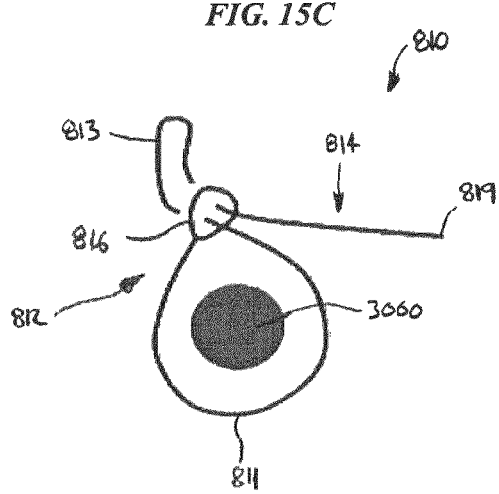
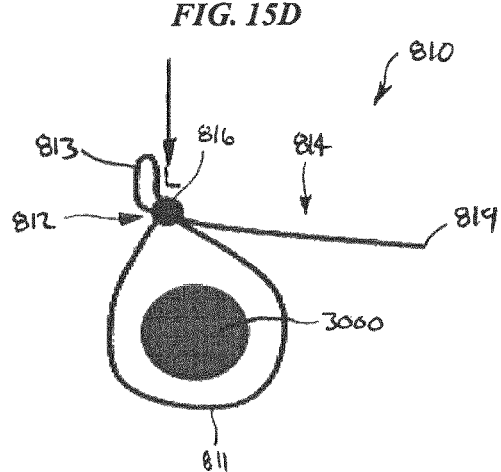
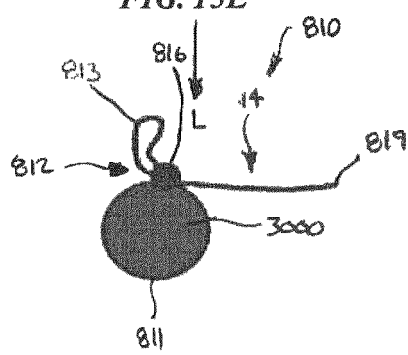
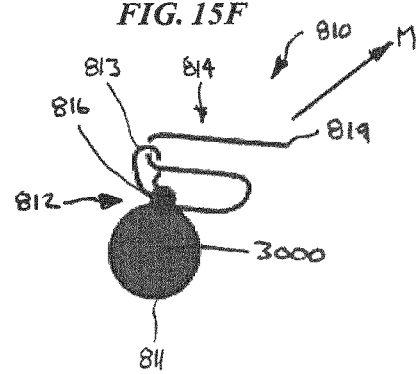
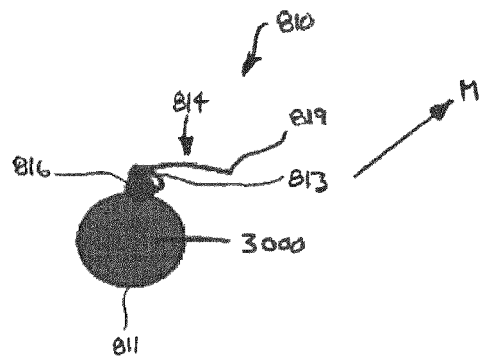

SYSTEMS, DEVICES, AND METHODS FOR SECURING TISSUE

CROSS-REFERENCE TO RELATED APPLICATION

This application claims priority to and is a continuation of U.S. patent application Ser. No. 14/713,566, filed May 15, 2015, and entitled "SYTEMS, DEVICES, AND METHODS FOR SECURING TISSUE," which claims priority to U.S. Pat. No. 9,060,763, filed May 7, 2012, and entitled "SYTEMS, DEVICES, AND METHODS FOR SECURING TISSUE," each of which is incorporated by reference in its entirety.

FIELD

The present disclosure relates to systems, devices, and methods for securing soft tissue to bone, and more particularly relates to securing soft tissue while minimizing or eliminating the tying of knots to tension and secure the tissue. The systems, devices, and methods provided herein can also be used to secure one or more objects, such as a bone fragment or tissue, and to draw two or more tissues together so they can be secured in a desired location.

BACKGROUND

A common injury, especially among athletes and people of advancing age, is the complete or partial detachment of tendons, ligaments, or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors, and tacks. Currently available devices for patients of advancing age can be particularly insufficient due to soft and weak bones leading to inadequate suture-to-anchor fixation.

Arthroscopic knot tying is commonly practiced in shoulder rotator cuff and instability procedures. Typically, an anchor loaded with suture is first attached to bone. The suture is normally slidably attached to the anchor through an eyelet or around a post, such that a single length of suture has two free limbs. One limb of the suture is passed through soft tissue to be repaired such as a tendon or labrum. The two ends of the suture are then tied to each other, thereby capturing the soft tissue in a loop with the anchor. Upon tightening the loop, the soft tissue is approximated to the bone via the anchor.

Surgeons typically tie the suture ends using a surgical sliding knot such as the Tennessee Slider or Duncan Loop. After advancing the knot distally to tighten the loop, a number of additional half hitches or other knots are tied in an effort to secure the new location of the sliding knot. The additional knots are needed because a conventional sliding knot used in current repair constructs does not provide the necessary protection against loosening or slippage, especially when tension is placed primarily on the limbs of the loop. The generally accepted practice is to follow the sliding knot with at least three reversed half hitches on alternating posts of the suture.

Before one or more half hitches or other knots can be added to the sliding knot, however, there exists a potential for the sliding knot to slip, that is, for the loop to enlarge as the tissue places tension on the loop. This has been referred to as "loop security" and can reportedly occur even in the hands of very experienced surgeons. Sometimes, even fully-tied knots may slip. In addition to this "loop security" problem, conventional knots typically have an overall size that can be obstructive or intrusive, especially in tight joints, which may damage cartilage or other tissue by abrasion with the knot.

Suture anchor systems with sliding and locking knots for repairing torn or damaged tissue include U.S. Pat. No. 6,767,037 by Wenstrom, Jr. Other suture anchor systems suited especially for meniscal repair are disclosed in U.S. Pat. No. 7,390,332 by Selvitelli et al. and are utilized in the OmniSpan™ meniscal repair system commercially available from DePuy Mitek Inc., 325 Paramount Drive, Raynham, Mass. 02767. Screw-type anchors normally require anchor attachment before operating sutures, which can lead to challenges related to the connection between the suture and the tissue.

There are a number of suture implant systems which proclaim to be "knotless," that is, to not require a surgeon to tie a knot during surgery. Many such systems control tension on tissue by the depth to which an anchor is driven into bone. U.S. Pat. Nos. 5,782,864 and 7,381,213 by Lizardi disclose certain types of suture anchors that capture a fixed-length loop of suture. Adjustable loop knotless anchor assemblies utilizing an anchor element inserted into a sleeve are described by Thal in U.S. Pat. Nos. 5,569,306 and 6,045,574 and in U.S. Patent Application Publication No. 2009/0138042. Other systems having clamps or other locking mechanisms include U.S. Pat. No. 5,702,397 by Goble et al. and U.S. Patent Application Publication No. 2008/0091237 by Schwartz et al. Present, so-called "knotless" designs, however, generally suffer from inadequate suture-to-anchor fixation and/or inadequate anchor-to-bone fixation, among other deficiencies.

It is therefore desirable to provide systems, devices, and methods for use in soft tissue repair that are robust and strong, yet minimize or eliminate the number and size of knots to be tied by a surgeon, particularly during arthroscopic repair procedures.

SUMMARY

Systems, devices, and methods are generally provided for securing soft tissue to bone, as well as for securing one or more objects, such as a bone fragment or tissue, and for drawing two or more tissues together so they can be secured in a desired location. In one embodiment a surgical repair construct includes a snare linkage, a collapsible loop, and a flexible suture pin, with the construct being configured to atraumatically pass through soft tissue to secure tissue in a knotless manner. The snare linkage can have a collapsible snare at a first end, a second end that is configured to receive the collapsible loop, and a connecting neck extending between the first and second ends. The collapsible loop can have a first end coupled to the second end of the snare linkage, a sliding knot, and a collapsible filament tail that extends from the sliding knot. The snare linkage can be made of a first suture filament, which can be braided or cannulated, and the collapsible loop can be made of a second suture filament. The flexible suture pin, which can be made of a third suture filament, can have a first portion that is removably disposed through the connecting neck and configured to prevent collapse of the snare. The pin can approximately maintain the size of the opening of the snare when it is present in the neck to prevent premature collapse of the snare.

In some embodiments, the snare can be configured such that the first suture filament is coaxially disposed through itself such that at least a portion of the connecting neck is a coaxial sliding neck that is slidable along another portion of the connecting neck. As a result, the coaxial neck can be movable towards the second end of the snare linkage to collapse the snare and movable away from the second end of the snare linkage to increase a size of the snare. The first portion of the suture pin can be removably disposed through the coaxial sliding neck, thus immobilizing the coaxial sliding neck. Further, a second portion of the removable suture pin can be disposed through a portion of the first suture filament that forms the collapsible snare. In such an embodiment, a stationary knot can be formed between the first and second portions of the suture pin at a position within a loop formed by the snare, and a terminal portion of the pin can extend beyond the loop.

In various embodiments, a thickness of the first filament can be in the range of about 20 gauge to about 32 gauge, a thickness of the second filament can be in the range of about 21 gauge to about 34 gauge, and/or a thickness of the third filament can be in the range of about 25 gauge to about 40 gauge.

In some other embodiments, the snare can be formed by a second sliding knot located proximate to the connecting neck. The sliding knot can be movable to collapse or expand a size of the snare. For example, the sliding knot can be movable away from the second end of the snare linkage to collapse the snare and movable towards the second end of the snare linkage to increase a size of the snare.

The second end of the snare linkage can include an eyelet, and the collapsible loop can be coupled to the snare linkage by the eyelet. Alternatively, the collapsible loop can be coupled to the second end of the snare linkage by passing a portion of the collapsible loop, e.g., the second suture filament, through a portion of the second end of the snare linkage, e.g., the first suture filament. In some embodiments, the construct can include a suture shuttle filament that can be coupled to the snare for use in advancing the snare linkage through tissue.

In some embodiments, a flexible sleeve can removably encapsulate at least a portion of the collapsible loop, including the sliding knot. The collapsible filament tail can be operable to collapse the collapsible loop when the sliding knot is moved towards the first end of the collapsible loop. The construct can also include a terminal filament tail formed from a portion of the second suture filament. The terminal filament tail can extend from the sliding knot, adjacent to the collapsible filament tail, and can be substantially stationary with respect to the sliding knot. The construct can also include an anchor having a filament engagement feature. In such embodiments, a portion of the collapsible loop can be slidably disposed around a portion of the filament engagement feature to couple the sliding knot to the anchor such that the sliding knot extends from one side of the anchor and the snare linkage extends from another side of the anchor.

In one exemplary embodiment of a surgical repair method, the method includes selecting a surgical repair construct having a snare linkage, a collapsible loop, and a flexible suture pin, fixing an anchor in bone in proximity to detached soft tissue, and passing the snare linkage and a portion of the collapsible loop through a portion of the detached soft tissue and around an engagement feature of the anchor. The resulting configuration can be one in which the snare linkage extends from one side of the anchor and the sliding knot extends from another side of the anchor. The selected surgical repair construct can include a number of features, for instance, the snare linkage can have a collapsible snare at a first end, a second end that is configured to receive the collapsible loop, and a connecting neck extending between the first and second ends. By way of further examples, the collapsible loop can have a first end coupled to the second end of the snare linkage, a sliding knot, and a collapsible filament tail extending from the sliding knot, and the flexible suture pin can have a first portion that is removably disposed through the connecting neck. The snare linkage can be made of a first suture filament, the collapsible loop can be made of a second suture filament, and the flexible suture pin can be made of a third suture filament.

The method can further include passing the second end of the collapsible loop, including the sliding knot, through the snare while capturing the detached tissue. The suture pin can be removed from the connecting neck, and the snare can be collapsed around the collapsible loop such that the snare is distal of the sliding knot. The snare can be advanced distally towards the bone until the snare is proximate to the tissue, and the collapsible loop can be collapsed by moving the sliding knot distally towards the bone to bring the tissue into proximity with the bone. The passing, collapsing, and advancing steps of the method can be effected without tying a knot in the first or second filaments. In some embodiments, the step of advancing the snare can occur before the step of collapsing the snare, while in other embodiments the step of advancing the snare can occur after the step of collapsing the snare. The step of advancing the snare distally can include tensioning the collapsible loop. Further, in some embodiments, advancing the snare distally by tensioning the collapsible loop can enable the snare to be advanced distally in an incremental fashion without slackening of the construct. The step of collapsing the collapsible loop can include tensioning the collapsible filament tail.

In some embodiments, the method can include passing the second end of the collapsible loop through a second portion of the detached soft tissue prior to passing the second end of the filament through the snare. A flexible sleeve can encapsulate at least a portion of the second end of the collapsible loop, including the sliding knot, during the passing steps. The sleeve can be removed from the surgical repair construct prior to collapsing the collapsible loop distally towards the bone. In some embodiments, a portion of the suture pin can include a needle attached thereto, and the suture pin can be passed through the detached soft tissue first to pull the snare linkage through the soft tissue. A portion of the suture pin can extend through the collapsible snare, a stationary knot can be disposed on a portion of the suture pin disposed inside a loop formed by the snare, and a terminal end of the suture pin can extend beyond the loop of the snare, with the needle being attached to the terminal end. In some other embodiments, a suture shuttle filament can be coupled to the snare, and the suture shuttle filament can be passed through the detached soft tissue first to pull the snare linkage through the soft tissue.

Another exemplary embodiment of a surgical repair method includes selecting a surgical repair construct having a snare linkage, a collapsible loop, and a flexible suture pin and fixing an anchor having an engagement feature in bone in proximity to detached soft tissue. The anchor can have a suture shuttle filament slidably coupled to the engagement feature with a first end of the suture shuttle filament extending from one side of the anchor and a second end of the suture shuttle filament extending from another side of the anchor. The selected surgical repair construct can include a number of features, for instance, the snare linkage can have a collapsible snare at a first end, a second end that is configured to receive the collapsible loop, and a connecting neck extending between the first and second ends. By way of further examples, the collapsible loop can have a first end coupled to the second end of the snare linkage, a sliding knot, and a collapsible filament tail extending from the sliding knot, and the flexible suture pin can have a first portion that is removably disposed through the connecting neck. The snare linkage can be made of a first suture filament, the collapsible loop can be made of a second suture filament, and the flexible suture pin can be made of a third suture filament.

The method can further include passing the first end of the suture shuttle filament through a portion of the detached soft tissue and coupling the second end of the collapsible loop to the first end of the suture shuttle filament. A force can be applied to the second end of the suture shuttle filament to pull the second end of the collapsible loop distally towards the bone and to the other side of the anchor. The resulting configuration can be one in which the snare linkage extends from one side of the anchor and the sliding knot extends from another side of the anchor. The second end of the collapsible loop, including the sliding knot, can be passed through the snare while capturing the detached tissue. The suture pin can be removed from the connecting neck, and the snare can be collapsed around the collapsible loop such that the snare is distal of the sliding knot. The snare can be advanced distally towards the bone until the snare is proximate to the tissue, and the collapsible loop can be collapsed by moving the sliding knot distally towards the bone to bring the tissue into proximity with the bone. The passing, collapsing, and advancing steps of the method can be effected without tying a knot in the first or second filaments. In some embodiments, the step of advancing the snare can occur before the step of collapsing the snare, while in other embodiments the step of advancing the snare can occur after the step of collapsing the snare. The step of advancing the snare distally can include tensioning the collapsible loop. Further, in some embodiments, advancing the snare distally by tensioning the collapsible loop can enable the snare to be advanced distally in an incremental fashion without slackening of the construct. The step of collapsing the collapsible loop can include tensioning the collapsible filament tail.

In some embodiments, the second end of the suture shuttle can be passed through a second portion of the detached tissue prior to applying a force to the second end of the suture shuttle filament to pull the second end of the collapsible loop distally towards the bone. The method can also include de-coupling the suture shuttle filament from the second end of the collapsible loop. A flexible sleeve can encapsulate at least a portion of the second end of the collapsible loop, including the sliding knot, during the passing steps. The sleeve can be removed from the surgical repair construct prior to collapsing the collapsible loop distally towards the bone.

In one exemplary embodiment of a surgical method, the method includes selecting a flexible surgical filament having a snare at a first end thereof and an opposed leading end and positioning the surgical filament substantially around an object to form a first loop. The leading end of the filament can be passed through the snare such that the leading end remains on one side of the snare and a second loop formed by the portion of the filament within the snare is on another side of the snare. The snare can be collapsed around the filament disposed therein to secure the first and second loops, with the first loop completely surrounding the object and the second loop being adjacent to the object. The first loop can then be collapsed around the object to engage the object with the filament. The leading end of the filament can be passed through the second loop, and then the second loop can be collapsed around the filament to secure the filament to the object. In some embodiments, the step of collapsing the first loop around the object can include pushing the collapsed snare towards the object. Further, in some embodiments, the step of collapsing the second loop around the filament can include tensioning the leading end of the filament.

BRIEF DESCRIPTION OF DRAWINGS

This invention will be more fully understood from the following detailed description taken in conjunction with the accompanying drawings, in which:

FIG. 4 is a schematic view of one exemplary embodiment of a snare of a snare linkage, the snare having a coaxial sliding neck and a flexible member disposed through the neck;

FIG. 5A is a schematic view of another exemplary embodiment of a snare of a snare linkage and a flexible member in which the snare has a coaxial sliding neck, this view illustrating how the flexible member can be disposed through the neck and the snare;

FIG. 5B is a schematic view of the snare linkage and flexible member of FIG. 5A, illustrating the flexible member disposed through the neck and the snare;

FIGS. 12A-12G are sequential views of one exemplary embodiment for using the surgical repair construct of FIG. 10 to secure tissue to bone;

FIGS. 13A-13D are sequential views of one exemplary embodiment for using the suture shuttle and anchor of FIG. 11 and the surgical repair construct of FIG. 9 to secure tissue to bone;

FIGS. 15A-15G are sequential views of one exemplary embodiment for using a surgical filament to secure an object;

DETAILED DESCRIPTION

Figure 1:
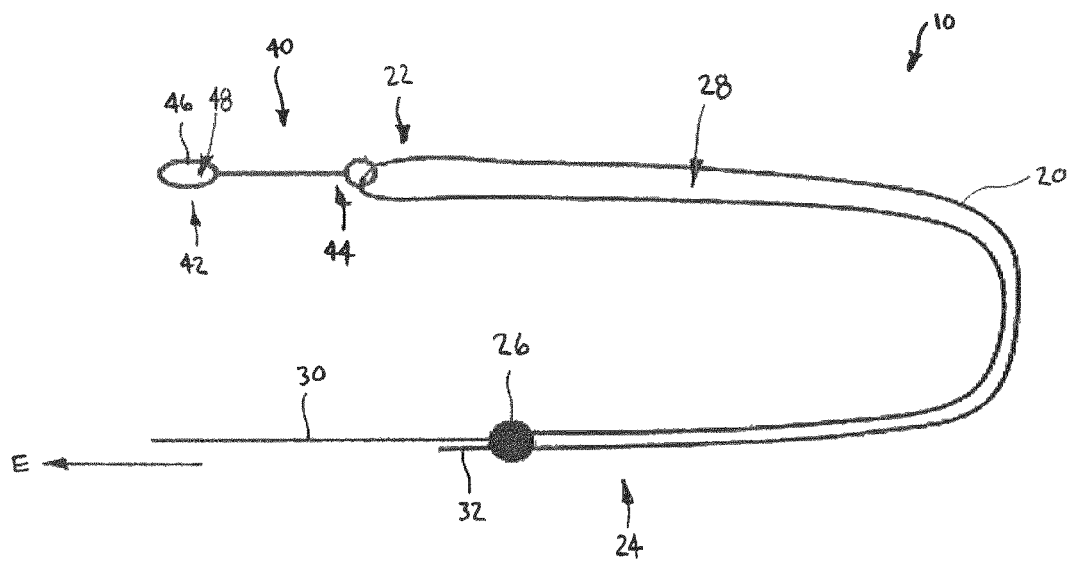
FIG. 1 is schematic view of one exemplary embodiment of a surgical repair construct.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Still further, to the extent arrows are used to describe a direction a component can be tensioned or pulled, these arrows are illustrative and in no way limit the direction the respective component can be tensioned or pulled. A person skilled in the art will recognize other ways and directions for creating the desired tension. Likewise, while in some embodiments movement of one component is described with respect to another, a person skilled in the art will recognize that other movements are possible. By way of non-limiting example, in embodiments in which a filament is passed through itself to form a coaxial sliding neck, movement described with respect to the inner portion (i.e., the coaxial sliding neck as discussed herein) moving relative to the outer portion can likewise involve movement of the outer portion with respect to the inner portion. Additionally, a number of terms may be used throughout the disclosure interchangeably but will be understood by a person skilled in the art. By way of non-limiting example, the terms suture and filament may be used interchangeably.

Systems, devices, and methods for soft tissue repair are generally provided and they generally involve the use of surgical filaments that are configured in a variety of manners to minimize and/or eliminate the tying of knots during a surgical procedure. The systems and devices described herein provide superior strength for use in a number of different surgical procedures, such as rotator cuff and instability repair procedures and other types of tendon and tissue repair procedures. They also allow for attachments that have a lower profile than existing systems and devices, which allows for the filaments to become associated with tissue, for instance by passing the filaments through the tissue or wrapping the filaments around the tissue, with minimal trauma to the tissue and less space being taken up by the overall construction. This results in systems and devices that can be associated with tissue atraumatically to secure the tissue in a knotless manner.

In addition to improving existing surgical procedures by providing repair constructs that are superior in strength and performance than existing constructs, the systems and devices provided herein also allow for both improved and new procedures for soft tissue repair. For example, the systems and devices provided herein can be used to advance tissue toward bone in an incremental fashion without the construct backlashing to cause the tissue to move away from the bone and/or to not be held tightly in place with respect to the bone. Further, the present disclosure provides for a number of different methods, some new and some improved, for fully securing objects, such as tissue and/or bone fragments, using a single filament and for securing tissue to bone or tissue to other tissue at desired locations using one or more filaments or repair constructs.

As shown by one exemplary embodiment of a surgical repair construct 10 in FIG. 1, the constructs of the present disclosure generally include a collapsible loop 20 having a first end 22 that is coupled to a snare linkage 40 and a second end 24 that includes a sliding knot 26 formed thereon. In the illustrated embodiment the snare linkage 40 has a snare 46 at a first end 42 thereof and a second end 44 configured to receive the first end 22 of the loop 20. The snare 46 includes an opening 48 that is configured to receive the second end 24 of the loop 20 and collapse around the second end 24 after it is disposed in the opening 48. The sliding knot 26 formed on the collapsible loop 20 can be operable to collapse a size of an opening 28 formed by the loop 20. In particular, the sliding knot 26 can be movable toward the first end 22 to collapse the loop 20, and it can also be movable away from the first end 22 to expand a size of the opening 28. In one embodiment, the collapsible loop 20 and the snare linkage 40 are each formed by different surgical filaments.

As shown, the collapsible loop 20 can include two tails, a collapsible tail 30, operable to move the sliding knot 26 towards the first end 22 in a ratchet-like or incremental manner, and a stationary terminal tail 32 configured to remain stationary with respect to the sliding knot 26. The construct 10 can be passed through one or more tissues such that passing the second end 24 through the snare 46 and both collapsing the snare 46 around the second end 24 and advancing the snare 46 distally (e.g., toward bone) can cause the tissue through which the construct 10 is disposed to be drawn toward a bone, an anchor, or other tissue to which the construct 10 is also coupled, as described in greater detail below. Because of the features of the constructs disclosed herein, many repair methods can be performed atraumatically and without tying knots to attach and move tissue to desired locations during the course of a surgical procedure.

Figure 2:
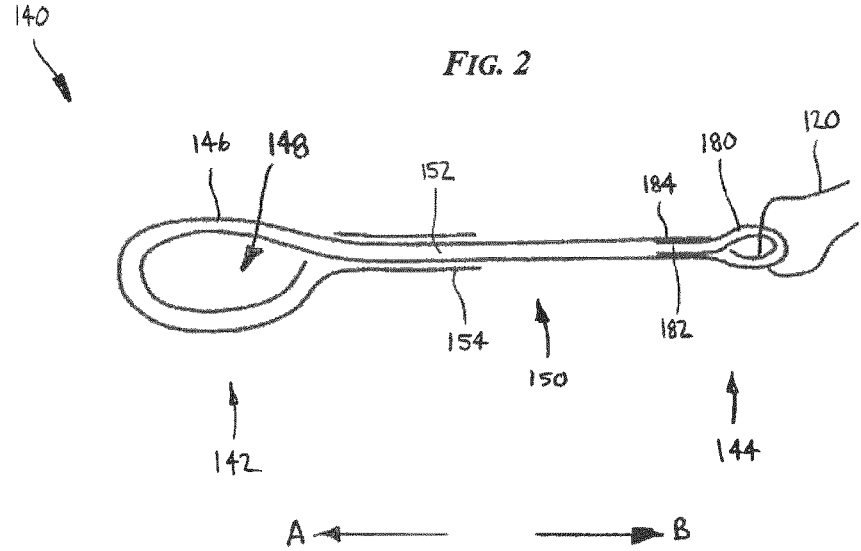
FIG. 2 is a schematic view of one exemplary embodiment of a snare linkage for use as part of a surgical repair construct.

FIG. 2 provides one exemplary embodiment of a snare linkage 140 for use as part of a surgical repair construct. A first end 142 of the snare linkage 140 can include a snare 146 that is configured to collapse under tension, a second end 144 of the snare linkage 140 can be configured to slidably couple to a collapsible loop 120 of the construct to allow relative motion between the linkage 140 and the loop 120, and a connecting neck 150 can extend between the two ends 142, 144. As shown in FIG. 2, the connecting neck 150 can be formed by a surgical filament having a coaxial sliding neck 152 that is slidable within a cannulated portion 154 of the connecting neck 150. Movement of the coaxial sliding neck 152 in approximately a first direction A, away from the second end 144, can expand a size of the snare opening 148, while movement of the coaxial sliding neck 152 in approximately a second direction B, toward the second end 144, can collapse the snare opening 148. A person skilled in the art will recognize that the coaxial sliding neck 152 moves with respect to the cannulated portion 154, and thus although the movement is described herein based on the movement of the coaxial sliding neck 152, the cannulated portion 154 can also be slid with respect to the coaxial sliding neck 152. Passing the filament that forms snare linkage 140 through itself to form the coaxial sliding neck 152 allows the snare linkage 140 to have a low profile that minimizes and/or eliminates the trauma associated with passing the snare linkage 140 through tissue, particularly in comparison to existing surgical repair constructs. Further, this construction can eliminate any sharp features that could be present in existing surgical repair constructs, which can present difficulties, including trauma, when trying to pass surgical repair constructs through tissue.

Figure 3A:
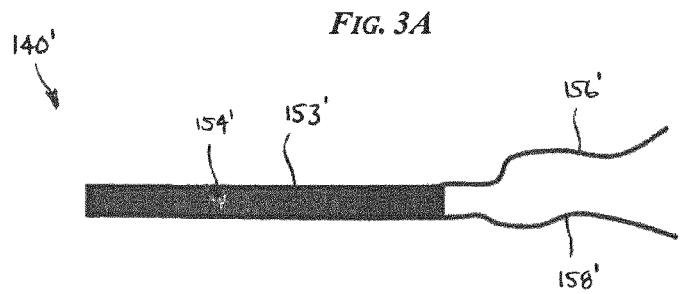
FIGS. 3A-3D are sequential views of one exemplary embodiment for forming a snare of a snare linkage in which the snare has a coaxial sliding neck.
Figure 3B:
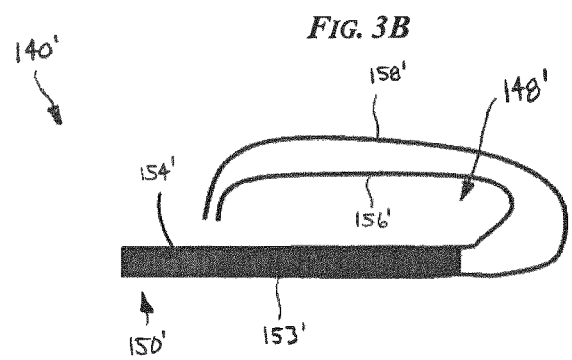
Figure 3C:
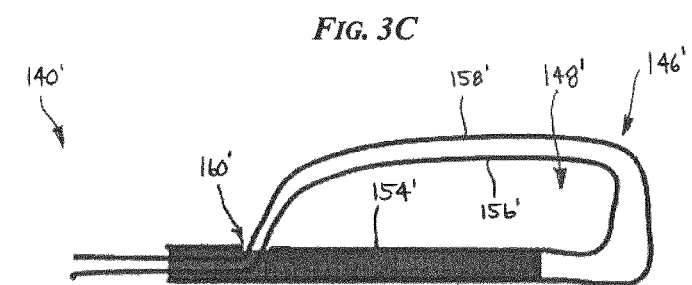
Figure 3D:
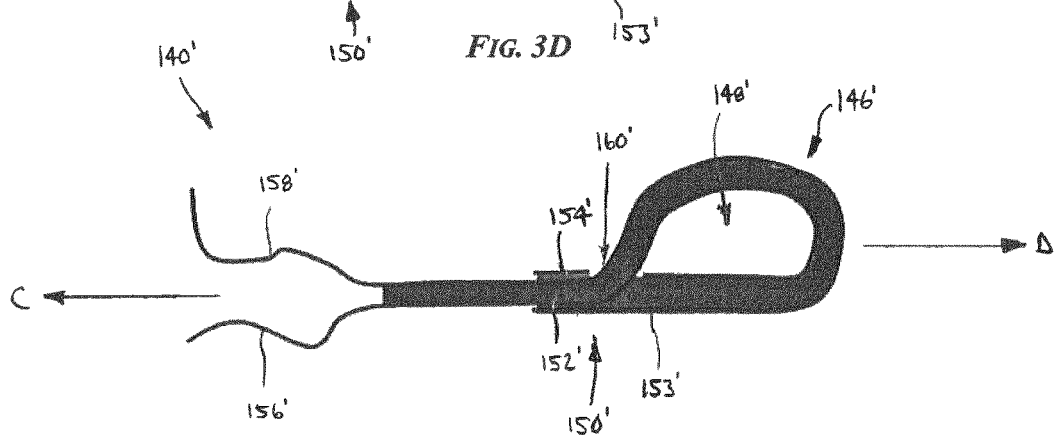

FIGS. 3A-3D illustrate one method of forming snare linkage 140' having a snare 146' and a coaxial sliding neck 152' for use in a surgical repair construct. In this exemplary embodiment, the snare 146' is formed from a bifurcated suture filament having a tubular portion 153' with a core removed therefrom to form a cannulated portion 154' and first and second terminal limbs 156', 158'. As shown in FIG. 3B, the terminal limbs 156', 158' can be curled back toward the tubular portion 153' to form a loop having an opening 148' that defines the snare 146'. As shown in FIG. 3C, a bore 160' can be formed on a side of the tubular portion 153' and the terminal limbs 156', 158' can be placed into the cannulated tubular portion 154' through the bore 160'. Ends of the terminal limbs 156', 158' can be fed through the cannulated portion 154', and as shown in FIG. 3D, the terminal limbs 156', 158' can be pulled distally (direction C in FIG. 3D) through the tubular portion 153' such that the tubular portion 153' is fed through itself. Accordingly, the snare 146' can be collapsed by tensioning the limbs 156', 158' in approximately a first direction C, and/or the coaxial portion of the tubular portion 153' that extends outside of the connecting neck 150', and the snare 146' can be expanded by applying a force to the snare 146' in approximately a second, opposite direction D, which pulls the limbs 156', 158' towards the snare 146'.

The sizes of the components of the snare linkage 140' can depend, at least in part, on the procedure in which it is being used, the components with which it is being used, and other factors recognized by those skilled in the art. In one embodiment the overall length of the snare linkage can be in the range of about 5 millimeters to about 50 millimeters, and in one embodiment it is about 36 millimeters. Further, in embodiments in which the snare linkage is formed of a filament having terminal limbs that extend through coaxially through a connecting neck, such as the embodiment shown in FIGS. 3A-3D, a length of the filament used to form the snare linkage can be in the range of about 15 centimeters to about 125 centimeters, and in one embodiment it is about 60 centimeters.

Snares can also be formed in a number of other manners known to those skilled in the art. For example, a number of different sliding knots can be used to form the snare of the snare linkage, including but not limited to a Buntline Hitch, a Tennessee Slider, a Duncan Loop, and a Hangman's Noose. To the extent the sliding knot used to form a snare affects the operation of the snare, for instance whether a limb is pulled through a knot to change the position of the knot or a knot is slid along a limb to change the position of the knot, a person skilled in the art would be able to adapt these types of knots for use with the teachings of the present invention without departing from the spirit of the present disclosure. As described herein, unless otherwise designated, a knot used to form a snare in a snare linkage is movable away from a second end of the snare linkage, i.e., away from the collapsible loop, to collapse the snare and towards the second end, i.e., towards the collapsible loop, to increase a size of the snare.

The snare linkage can be made of a variety of materials, but in one exemplary embodiment the snare linkage is formed using a surgical filament, such as a cannulated filament, a braided filament, and a mono filament. The type, size, and strength of the filament can depend, at least in part, on the other materials of the system, including the material(s) of the collapsible loop with which it is used, the tissue and other components through which it will be passed or coupled to, and the type of procedure in which it is used. In one exemplary embodiment the snare linkage is formed from a #2 filament (about 23 gauge to about 24 gauge), such as an Orthocord™ filament that is commercially available from DePuy Mitek, Inc. or an Ethibond™ filament that is commercially available from Ethicon, Inc., Route 22 West, Somerville, N.J. 08876. The cores of these filaments can be removed to form a cannulated configuration if desired. The thickness of the snare linkage should provide strength in the connection but at the same time minimize the trauma caused to tissue through which it passes. In some embodiments the snare linkage can have a size between about a #5 filament (about 20 gauge to about 21 gauge) and about a #3-0 filament (about 29 gauge to about 32 gauge). The Orthocord™ 2 filament can be useful because it has a braided configuration, which allows other components, such as flexible members or collapsible loops as discussed below, to pass through subcomponents of the braid without causing damage to the filament. Filaments configured to allow for a cannulated configuration, such as by removing a core therefrom or having a pre-formed cannulated configuration, can also be used to form the snare linkage. Orthocord™ suture is approximately fifty-five to sixty-five percent PDS™ polydioxanone, which is bioabsorbable, and the remaining thirty-five to forty-five percent ultra high molecular weight polyethylene, while Ethibond™ suture is primarily high strength polyester. The amount and type of bioabsorbable material, if any, utilized in the filaments of the present disclosure is primarily a matter of surgeon preference for the particular surgical procedure to be performed.

In use, the length of portions of the snare linkage, and in particular the snare and the connecting neck, can change as the snare is collapsed. In one exemplary embodiment, a diameter of the snare opening in an uncollapsed position is in the range of about 2 millimeters to about 15 millimeters, and in one embodiment it is about 10 millimeters while a length of the connecting neck when the snare is in an uncollapsed configuration is in the range of about 0 millimeters (excluding the length of the connecting neck) to about 45 millimeters (excluding the length of the connecting neck), and in one embodiment it is about 5 millimeters (excluding the length of the connecting neck). A length of the neck after the snare is collapsed, on the other hand, can be in the range of about 3 millimeters (excluding the length of the connecting neck) to about 45 millimeters (excluding the length of the connecting neck), and in one embodiment is about 27 millimeters (excluding the length of the connecting neck).

Because the connecting neck, and particularly the sliding neck 152 and the cannulated portion 154, can allow the snare to both expand and contract, a flexible member, such as a suture pin, can be removably disposed across the neck to prevent unintentional movement of the snare as the snare passes through an obstruction, such as tissue. In embodiments in which a connecting neck 250 (FIG. 4) includes a coaxially sliding neck 252, such as in the snare 246 of a snare linkage 240 illustrated in FIG. 4, a flexible member 270 can extend across the neck 250 to immobilize the coaxially sliding neck 252 with respect to the connecting neck 250. Once the snare 246 is passed through the obstruction and the risk of unintentional and premature expansion or collapse is reduced, the flexible member 270 can be removed. The use of a flexible member of the type described herein to prevent unintentional collapse of the snare in tissue repair procedures is advantageous as it can allow the snare linkage to be passed atraumatically through tissue while still preventing unintentional collapse of a snare.

In another embodiment, shown in FIGS. 5A and 5B, a flexible member 370 can both immobilize a snare 346 of a snare linkage 340 and serve as a suture shuttle to guide the snare linkage 340 through obstructions during the course of a procedure. As shown in FIG. 5A, a first end 372 of the flexible member 370 can be passed across connecting and coaxial necks 350, 352 of the snare linkage 340 so that a first portion of the flexible member 370 is disposed through the neck 350, while a second end 374 of the flexible member 370 is passed through and disposed in the snare 346. A protrusion 376, for instance a stationary knot that can be pre-formed or formed or modified during a procedure, can be disposed on the flexible member 370 at a location between the first and second ends 372, 374. The protrusion 376 can serve to maintain the flexible member 370 in a coupled arrangement with the snare linkage 340, and as shown in FIG. 5B, the protrusion 376 can be disposed within the opening or loop 348 formed by the snare 346, abutting a surface of the snare, with a terminal portion 378 extending through and beyond the loop 348 for use as a shuttle. Optionally, a needle or similar tool or device can be coupled to the terminal portion 378 to assist in threading the snare linkage 340 through tissue.

Other configurations in which a flexible member is used as both a suture pin and a suture shuttle are also possible, depending, at least in part, on the configuration of the snare linkage and obstructions though which the snare linkage will be passed, without departing from the spirit of the present disclosure. For example, the flexible member 370 can be disposed through another portion of the connecting neck 350 or a different portion of the snare 346. One benefit of using a flexible member for both maintaining a snare shape and shuttling the snare linkage is that it can improve filament management by limiting the number of filaments used in a procedure. Further, such a construction allows for a single action to remove both the pin and the shuttle from the linkage, such as applying tension to a second terminal end 379 of the flexible member 370 to decouple the flexible member 370 from the snare linkage 340.

Figure 6:
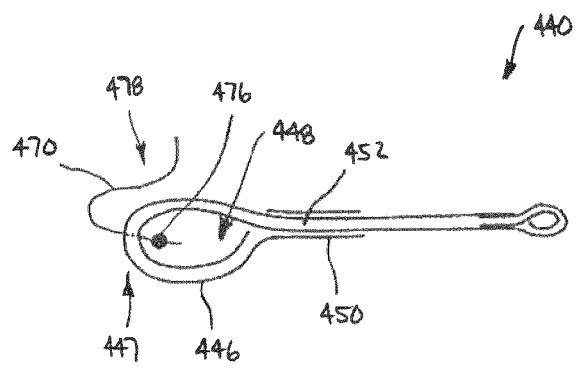
FIG. 6 is a schematic view of an exemplary embodiment of a snare of a snare linkage and a flexible member in which the snare has a coaxial sliding neck and the flexible member is disposed through the snare.
Figure 7:
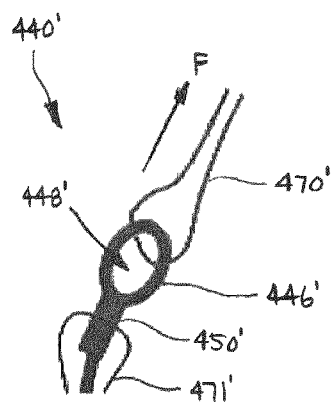
FIG. 7 is a schematic view of another exemplary embodiment of a snare of a snare linkage and a flexible member in which the flexible member is disposed through a neck of the snare and a suture shuttle is looped through the snare.

In still other embodiments a flexible member can be used primarily for the purpose of shuttling the snare linkage through obstructions. FIGS. 6 and 7 illustrate two examples of ways a flexible member 470, 470' can be coupled to a snare linkage 440, 440' for shuttling purposes. As shown in FIG. 6, the flexible member 470 is passed across a top portion 447 of the snare 446, with a protrusion 476 being formed on the flexible member 470 to maintain a coupling between the flexible member and the snare assembly during shuttling. The protrusion 476 can be disposed within the opening or loop 448, abutting a surface of the loop, with a terminal portion 478 extending through and beyond the loop 448 for use as a shuttle. A needle or similar tool or device can optionally be coupled to the terminal portion 478 to assist in threading the snare linkage 440 through tissue. Although not illustrated, it can be helpful to include another flexible member disposed across a connecting neck 450 of the snare linkage 440 to immobilize a coaxially sliding neck 452 disposed therein while the snare linkage 440 is being shuttled through obstructions.

As shown in FIG. 7, a first flexible member 470' is coupled to a snare linkage 440' by looping the flexible member 470' through a snare 446', and a second flexible member 471' is disposed across a connecting neck 450' to immobilize the neck 450' while the snare linkage 440' is being shuttled through obstructions. In the absence of a flexible member 471' across the neck 450', or other suture pin mechanism in its place, tension applied to the first flexible member 470' in approximately a direction F to shuttle the snare linkage 440' through obstructions would cause the size of the snare opening 448' to decrease.

The flexible member(s) for any of the embodiments described herein can be made of a variety of materials, but in one exemplary embodiment it is a surgical filament that is separate from the surgical filament that forms the snare linkage. In some embodiments the flexible member is formed using a surgical filament, such as a cannulated filament, a braided filament, and a mono filament. The type, size, and strength of the filament can depend, at least in part, on the other materials of the system, including the material(s) of the neck through which it will pass, the obstructions through which the snare will pass, how the filament is being used (e.g., as a suture pin, as a suture shuttle, or as a joint suture pin and suture shuttle), and the type of procedure in which it is used. In one exemplary embodiment the flexible member is formed from a #2-0 filament (about 28 gauge), such as an Orthocord™ filament that is commercially available from DePuy Mitek, Inc. or Ethibond™ filament available from Ethicon Inc. Generally the flexible member is relatively thin to minimize any trauma to tissue through which it passes, and typically the flexible member is thinner than the snare linkage. In some embodiments the flexible member can have a size between about a #1 filament (about 25 gauge to about 26 gauge) and about a #6-0 filament (about 38 gauge to about 40 gauge). A length of the flexible member can be in the range of about 1 centimeter to about 100 centimeters. In one embodiment in which the flexible member is only being used as a suture pin it can have a length of about 1 centimeter. In one embodiment in which the flexible member is used as both a suture pin and a suture shuttle it can have a length of about 50 centimeters. In one embodiment in which the flexible member is only being used as a suture shuttle it can have a length of about 100 centimeters.

Figure 8:
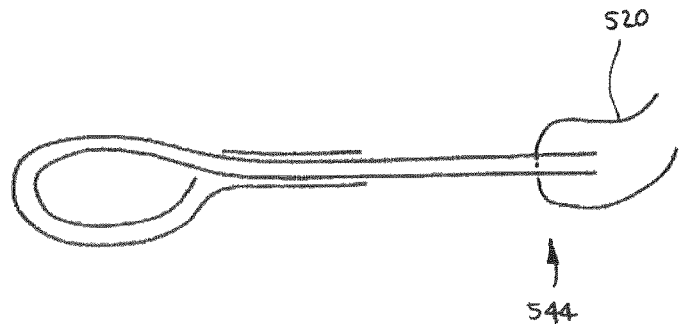
FIG. 8 is a schematic view of another exemplary embodiment of a snare linkage for use as a part of a surgical repair construct.

A person skilled in the art will appreciate that a number of different configurations can be used to slidably mate a collapsible loop with a snare linkage. Two such embodiments are shown in FIGS. 2 and 8. As shown in FIG. 2, the second end 144 of the snare linkage 140 includes an eyelet 180 configured to receive the collapsible loop 120. The eyelet 180 is generally circular in shape, and can generally have a substantially fixed diameter. The eyelet 180 can be formed in any number of ways, but in one embodiment in which the snare linkage 140 is formed from a cannulated or braided surgical filament, a first portion 182 of the filament can be passed through a second portion 184 to form the eyelet 180, similar to the formation of the snare 146 at the first end 142. However, to maintain a substantially fixed diameter, the first portion 182, which serves as a coaxially sliding neck, can be fixed with respect to the second portion 184, which serves as an outer neck. Any number of techniques can be used to fix the location of the sliding neck 182, including using an adhesive, heat bonding the filament, or disposing a pin or other fasteners thereacross. By passing the filament through itself to form the eyelet 180, the snare linkage 140 maintains a low profile at the second end 144. While a size of the eyelet can depend, at least in part, on the other components of the construct, the obstructions through which the snare linkage will pass, and the type of procedure in which it is used, a diameter of the eyelet can be in the range of about 1 millimeter to about 10 millimeters, and in one embodiment it is about 3 millimeters.

FIG. 8 provides an alternative configuration for a second end 544 of a snare linkage 540. As shown, a collapsible loop 520 is coupled to the snare linkage 540 by passing the loop 520 through the filament at the second end 544. The filament that forms snare linkage 540 can be a cannulated filament, a braided filament, or a mono filament that enables the loop 520 to pass through the filament and maintain a sliding engagement therewith without causing damage to filament of the snare linkage 540 or the loop 520. One skilled in the art will appreciate that second end 544 of the filament can be treated to prevent unintended fraying. For example, the second end of the filament can be heat bonded, coated, or otherwise treated to prevent fraying. Alternative configurations and materials beyond those provided in FIGS. 2 and 8 can also be used by those skilled in the art to allow for a sliding engagement between the second end of the linkage and the collapsible loop.

Although in the illustrated embodiments the snare is part of a separately formed snare linkage, in other embodiments a single filament can be used to form both the snare and the collapsible loop. Other techniques can also be used to form the snare and loop, including those discussed in U.S. patent application Ser. No. 13/218,810 filed Aug. 26, 2011, and entitled "SURGICAL FILAMENT SNARE ASSEMBLIES," the content of which is incorporated by reference herein in its entirety.

The collapsible loop 20 illustrated in FIG. 1 can generally be a flexible elongate member having a first end 22 coupled to the snare linkage 40 and a second end 24 closed by a sliding knot 26. The sliding knot 26 allows the loop 20 to be collapsed as desired, and thus when a portion of the loop 20 is coupled to or passed through tissue, collapsing the loop 20 can tension the tissue to draw it toward a desired location. As shown in FIG. 1, as the knot 26 is moved toward the first end 22, the loop 20 collapses, and as the knot 26 is moved away from the first end 22, the size of the opening 28 of the loop 20 increases. The sliding knot 26 can be formed in a variety of ways using a variety of techniques well known to those skilled in the art. Non-limiting examples of the types of knots that can be used as the loop's sliding knot include a Buntline Hitch, a Tennessee Slider, a Duncan Loop, a Hangman's Noose, and a loop having a coaxial sliding neck.

As shown in FIG. 1, the loop 20 can also have a collapsible tail 30 and a stationary terminal tail 32 that extend from the sliding knot 26. The tails 30, 32 can be terminal ends of two limbs of a filament used to form the sliding knot 26 that completes the collapsible loop 20. The collapsible tail 30 can be operable to tension and collapse the loop 20 by moving the sliding knot 26 towards the loop first end 22. More particularly, applying tension to the collapsible tail 30 in approximately the direction E can cause the knot 26 to slide distally toward the first end 22. As a result, the sliding knot 26 can move in a ratchet-like or incremental fashion such that the knot 26 moves toward the first end 22 without backlashing and causing the collapsible loop 20 to increase in size. When tension is not applied, the location of the sliding knot 26 remains substantially fixed, and further tensioning of the collapsible tail 30 can cause further distal movement of the knot 26 until either the tension is released or an obstruction precludes further distal movement of the knot 26. The self-locking capabilities provided by this sliding knot 26 that result from the overall formation of the construct 10 are beneficial at least because of the ability to incrementally advance the knot 26 without backlashing.

As shown, the stationary terminal tail 32 is adjacent to the collapsible filament tail 30 and is stationary with respect to the sliding knot 26. In the illustrated embodiment the stationary terminal tail 32 is shorter than the collapsible tail 30, but in other instances it can be the same length as or even longer than the collapsible tail 30. A longer stationary tail 32 can provide some beneficial aspects. For example, in some embodiments, a long stationary tail 32 can be used as a suture shuttle to pass the collapsible loop 20 through tissue. Using the stationary tail 32 as a shuttle can prevent a premature collapse of the loop 20. In such embodiments, a needle or similar tool or device can optionally be coupled to the stationary tail 32 to assist in threading the tail 32 through tissue. Further, once a procedure is completed using the construct 10 that has a longer stationary tail 32, one or more half-hitches can optionally be formed on the stationary tail 32 to provide additional system strength. Such half-hitches can also be formed on the collapsible tail 30 if desired for additional strength. Still further, longer stationary and collapsible tails 32, 30 can be used in conjunction with other types of procedures, such as double row procedures, as described in greater detail below.

Similar to the other components of the surgical repair construct, the flexible loop can be made of a variety of materials, but in one exemplary embodiment it is a surgical filament. The surgical filament that forms the collapsible loop is typically a separate filament than what is used to form the snare linkage or the flexible member. Further, the filament of the collapsible loop can be any suitable suture material such as a cannulated filament, a braided filament, and a mono filament. The type, size, and strength of the filament can depend, at least in part, on the other materials of the system, including the materials of any snare linkage or bone anchor with which the loop may be associated, the obstructions through which the loop will pass, and the type of procedure in which it is used. In one exemplary embodiment the flexible loop is formed from a #0 filament (about 26 gauge to about 27 gauge), such as an Orthocord™ filament that is commercially available from DePuy Mitek, Inc or Ethibond™ filament available from Ethicon, Inc. Generally the collapsible loop is relatively thin to minimize any trauma to tissue through which it passes, and can typically the loop is thinner than the snare linkage. In some embodiments the collapsible loop can have a size between about a #4 filament (about 21 gauge to about 22 gauge) and about a #4-0 filament (about 32 gauge to about 34 gauge). A length of the loop in its uncollapsed configuration can be in the range of about 2 centimeters to about 60 centimeters, and in one embodiment it can be about 40 centimeters. Still further, a diameter of the sliding knot of the loop will depend, at least in part, on the size of the filament used to form it, the type of sliding knot that it is, and the type of procedure with which it will be used. In one exemplary embodiment a diameter of the sliding knot can be in the range of about 0.5 millimeters to about 3 millimeters, and in one embodiment it can be about 1 millimeter.

Figure 9:
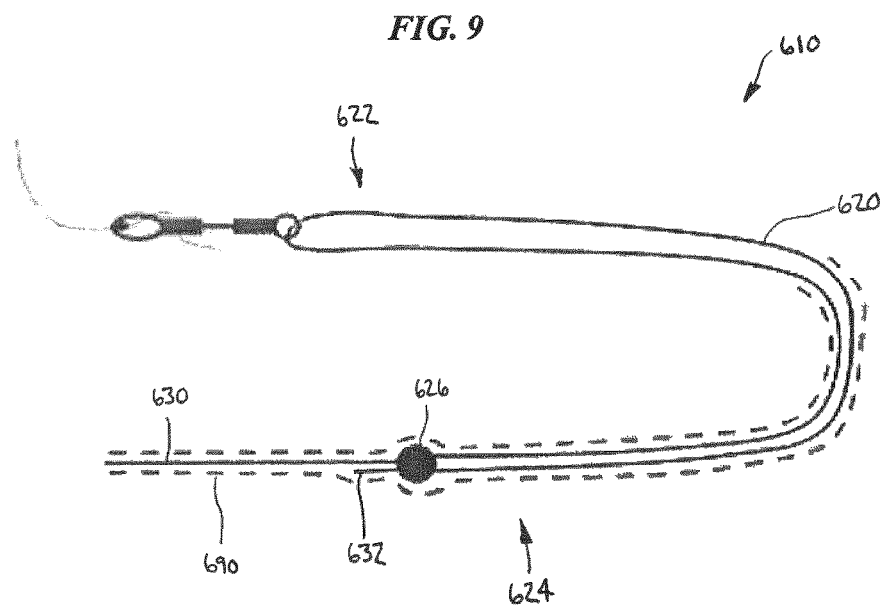
FIG. 9 is a schematic view of another exemplary embodiment of a surgical repair construct.

Optionally, a flexible sleeve can be provided for encapsulating at least a portion of a collapsible loop. As shown in FIG. 9, in one embodiment of a repair construct 610, a sleeve 690 can be disposed around collapsible and stationary terminal tails 630, 632, a sliding knot 626, and a portion of the loop 620 at a second end 624, extending toward a first end 622. The sleeve 690 can have a generally cylindrical configuration and can be flexible to allow it to bend as shown in various embodiments provided herein. The sleeve 690 can be useful when passing the construct 610 through obstructions such as tissue for a number of reasons. The sleeve 690 can protect the knot 626 from being unintentionally tightened when it passes through an obstruction. Further, the sleeve 690 can be configured to have a smoother surface that is better configured to pass through tissue than a knot, thus easing trauma caused by passing the construct 610 through tissue. Still further, because the sleeve 690 can encapsulate a plurality of filament limbs, the sleeve 690 can ease filament management by maintaining the filaments within the enclosed sleeve 690. The sleeve 690 can be removable, and it is typically removed prior to collapsing the loop 620 so that the sleeve 690 does not interfere with movement of the sliding knot 626.

FIG. 9 illustrates only one of many possible configurations of which portions of the construct 610 can be encapsulated by the sleeve 690. In some embodiments, one or both of the collapsible and stationary terminal tails 630, 632 can extend beyond the sleeve 690. Alternatively, the sleeve 690 can extend a length beyond terminal ends of the collapsible and stationary terminal tails 630, 632 such that a portion of the sleeve 690 is empty. A configuration of this nature can aid a surgeon in pulling the construct 610 through a portion of the body by providing extra length onto which he or she can grasp. Preferably the sleeve 690 can extend outside of a body and a cannula placed in the body once the construct 610 is implanted so the sleeve 690 can be easily removed.

The sleeve can be made from a wide variety of biocompatible flexible materials, including a flexible polymer or it can be another filament. In one embodiment, the sleeve is made of a polymeric material. In another embodiment, the sleeve is a flexible filament, such as a braided suture, for example Ethibond™ #0 filament or Orthocord™ #2 filament, which is typically braided at sixty picks per 2.54 centimeters. For use as a sleeve, a more relaxed braid of approximately thirty to forty picks per 2.54 centimeters is preferred, more preferably about 36 picks per 2.54 centimeters. If the sleeve material is formed about a core, preferably that core is removed to facilitate insertion of the filament limbs, which may themselves be formed of typical suture such as Orthocord™ #0 suture or #2 suture braided at sixty picks per 2.54 centimeters. Additional convenience can be provided by perceptible indicators on the sleeve such as different markings, colors, diameters, braid or design patterns, or other tactile or visual indicia, especially if multiple tissue attachments or anchors are utilized.

A length and diameter of the sleeve can depend, at least in part, on the size and configuration of the components of the construct with which it is used, the obstructions through which the sleeve may pass, and the surgical procedure in which it is used. In any event, the sleeve is typically of a size such that it can pass atraumatically through tissue. In embodiments in which the sleeve is a filament, a size of the sleeve can be in the range of about a #5 filament (about 20 gauge to about 21 gauge) to about a #2-0 filament (about 28 gauge), and in one embodiment the size can be about a #0 filament (about 26 gauge to about 27 gauge). A person having skill in the art will recognize comparable diameter sizes that can be used in instance in which the sleeve is made of a polymeric or other non-filament material. The sleeve can have a length in the range of about 10 centimeters to about 60 centimeters, and in one embodiment it has a length of about 40 centimeters.

Figure 10:
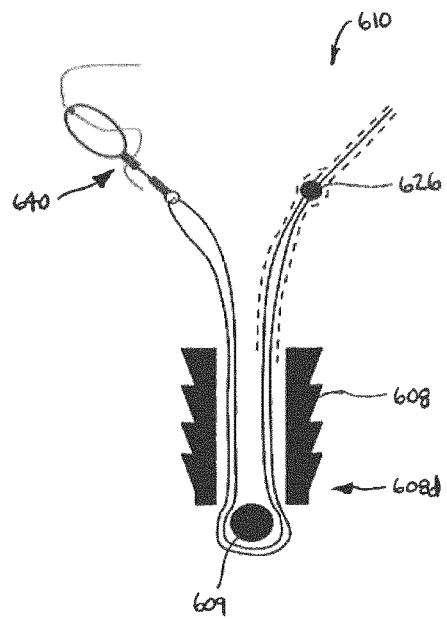
FIG. 10 is a schematic view of the surgical repair construct of FIG. 9 coupled to an anchor.

FIG. 10 illustrates one exemplary embodiment of the repair construct 610 of FIG. 9 coupled to a bone anchor 608. One skilled in the art will appreciate that a variety of bone anchor types can be used in conjunction with the constructs provided herein. However, for purposes of illustration, anchor 608 is a Healix Ti™ anchor that is commercially available from DePuy Mitek, Inc. The anchor 608 can include a filament engagement feature 609, which can be on any part of the anchor, but in the exemplary embodiment is at a distal end 608d of the anchor 608 and allows the construct 610 to be slidably engaged with the anchor 608. Regardless of the type of anchor used, the construct 610 should be slidingly coupled to the anchor 608 by way of the filament engagement feature 609 such that the snare linkage 640 extends from one side of the anchor 608 and the sliding knot 626 extends from the other side of the anchor 608. The use of this construct 610 is described below with respect to FIGS. 12A-12G.

Figure 11:
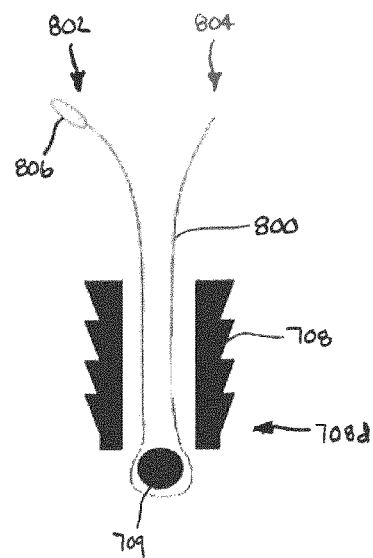
FIG. 11 is a schematic view of a suture shuttle coupled to an anchor.

FIG. 11 illustrates one exemplary embodiment of a suture shuttle 800 coupled to a bone anchor 708. Again, virtually any type of bone anchor can be used in conjunction with the shuttles and constructs provided herein, but the illustrated anchor 708 is a Healix Ti™ anchor that is commercially available from DePuy Mitek, Inc. The anchor 708 can include a filament engagement feature 709, which can be at a distal end 708d of the anchor 708 and which allows the shuttle 800 to be slidably engaged with the anchor 708. As shown, the shuttle 800 is slidingly coupled to the anchor 708 at the filament engagement feature 709 such that a first end 802 of the shuttle 800 extends from one side of the anchor 708 and a second end 804 of the shuttle 800 extends from the other side of the anchor 708. The first end 802 can be configured to be coupled to a repair construct, such as the repair construct 610 of FIG. 9. As shown, the first end 802 includes a collapsible snare 806, but any other suitable coupling mechanism can be used at the first end 802 without departing from the spirit of the present disclosure. For example, the first end 802 can include a clip or a like element to clamp around a repair construct. Once the repair construct 610 is coupled to the first end 802, the second end 804 can be used to position the repair construct 610 in a desired location as described below with respect to FIGS. 13A-13D.

One exemplary embodiment of a method for performing a rotator cuff repair using the repair construct illustrated in FIG. 10 is illustrated in FIGS. 12A-12G. A surgical opening can be formed through skin 1000 and a cannula can be passed therethrough to create a surgical repair site in a manner well known to those skilled in the art. Although cannulas are often used to define a channel through which the procedure can be performed, the cannula is not shown in FIGS. 12A-12G for ease of illustration. Accordingly, to the extent the figures show components of the systems and devices passing through skin 1000, these components would typically be extending through the cannula, which itself is passed through the skin 1000. Further, although the devices and methods described herein are particularly useful for minimally invasive surgery, such as arthroscopic surgery, they can also be used in open surgical procedures.

Figure 12A:
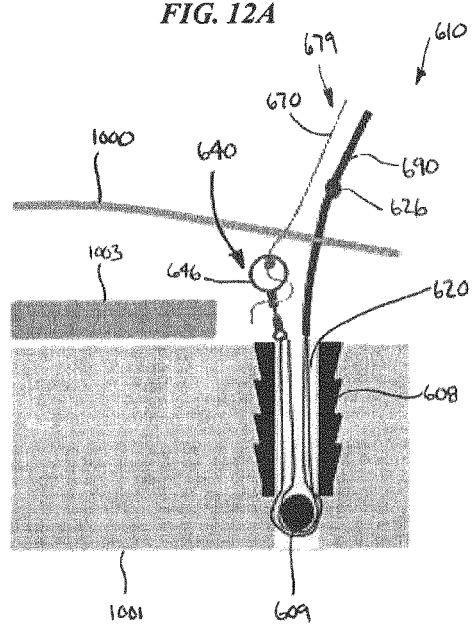

As shown in FIG. 12A, the anchor 608 shown in FIG. 10 can be fixated into bone 1001 using ordinary techniques, such as with a driver to screw or tap the anchor 608 into place. In the illustrated embodiment the construct 610, which includes a flexible member 670 that serves as both a suture pin and a shuttle, is already coupled thereto, although in other embodiments the construct 610 can be slidingly coupled to the anchor 608 after the anchor 608 is positioned at its desired location.

Figure 12B:
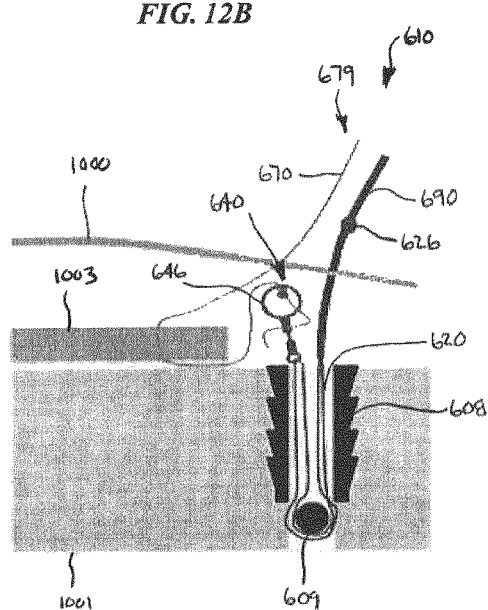

As shown in FIGS. 12B and 12C, a terminal portion 679 of the flexible member 670 can be passed into and through tendon 1003 detached from bone 1001 to pull the snare linkage 640, and a portion of the collapsible loop 620, through the tendon 1003. Optionally, a needle or similar tool or device can be coupled to the terminal portion 679 to assist with threading the construct 610 through the tendon 1003. Likewise, other shuttling techniques, including those described herein and those known to a person skilled in the art, can also be used to pass the snare linkage 640 through and/or around the tendon 1003. The other end of the construct 610 on which the sliding knot 626 is disposed can also pass through the tendon 1003 at a second location on the tendon 1003. As shown, the optional sleeve 690 can be disposed around the limbs 630, 632, the sliding knot 626, and a portion of the loop 620, thereby easing any trauma caused by passing this portion of the construct 610 through the tendon 1003 and assisting with management of the filament limbs. As a result, on one side of the anchor 608 is the snare linkage 640 that has been passed through the tendon 1003 at a first location and is accessible to the surgeon outside of the body, and on the other side of the anchor 608 is the sliding knot 626 that has been passed through the tendon 1003 at a second location and is accessible to the surgeon outside of the body.

As shown in FIG. 12D, a portion of the loop second end 624 can be passed through the snare 646 such that the snare 646 is distal of the sliding knot 626, thereby allowing the tendon 1003 through which the construct 610 is disposed to be captured. The flexible member 670 can be removed from the snare linkage 640, and the snare 646 can be collapsed or dressed around the portion of the second end 624 that is disposed therethrough, with the snare 646 remaining distal of the sliding knot 626. The flexible member 670 can actually be removed from the snare linkage 640 any time after it has been passed through any tissue such that its purposes of serving as a shuttle for the construct 610 and a pin to prevent unintentional collapse of the snare 646 are no longer desired.

As shown in FIG. 12E, tension can be applied to the second end 624 by pulling approximately in a direction G, thereby causing the collapsed snare 646 to slide distally toward the tendon 1003 in a zip-line like manner until the snare 646 is adjacent to the tendon 1003. Alternatively, tension can be applied to the second end 624 before the snare 646 is dressed and after the snare 646 is adjacent to the tendon 1003, or some combination of the two actions can be used, such as partially dressing the snare 646 before zip-lining it toward the tendon 1003. As shown in FIG. 12E, when the snare 646 is collapsed, additional filament that was previously part of the snare 646 forms an elongated connecting neck 651 between the first and second ends of the snare linkage 640. As shown, a portion of this elongated connecting neck 651 can become disposed around the filament engagement feature 609.

If a sleeve 690 is included as part of the construct 610, it can be removed once it is used to assist in passing the second end of the construct 610 through tissue. However, it can be helpful to keep the sleeve 690 disposed around a portion of the loop second end 624 to prevent unintentional movement of the knot 626, to continue helping to manage filament limbs, and to help in zip-lining the snare 646 toward the tendon 1003 because there is typically less friction created by the sleeve 690 as opposed to the filament that the sleeve 690 encapsulates. As shown in FIG. 12F, once the sleeve 690 is no longer desired, it can be removed from the construct 610 to expose the sliding knot 626 and the collapsible tail 630. Tension can be applied to the collapsible tail 630 by pulling approximately in the direction H, thereby causing the knot 626 to advance distally towards the tendon 1003 so that it can be adjacent to the snare 646 and in turn bring the tendon 1003 into proximity with the bone 1001, as shown in FIG. 12G. The configuration of the construct 610 allows the knot 626 to be advanced in an incremental, ratchet-like fashion when the collapsible tail 630 is pulled in the direction H without the risk of reversing the progress of the knot 626 as a result of slipping backward, sometimes referred to as backing out, backlashing, or slackening of the filament. Alternatively, in an embodiment in which no sleeve is used and thus the knot 626 is free to slide, the snare 646 and the loop 620 can be collapsed at the same time by applying tension to the collapsible tail 630 approximately in the direction H.

As shown in FIG. 12G, optionally, one or more half-hitches 631 can be added to the filament adjacent to the sliding knot 626 to provide additional strength once the filaments have been finally positioned to approximate tissue. The half-hitches 631 can be formed on either or both of the collapsible and stationary terminal tails 630, 632. The formation of one or more half-hitches, however, can hinder the ability for the collapsible tail 630 to provide the incremental movement of the sliding knot 626. Accordingly, in instances in which multiple constructs are used together as part of a procedure, it may be desirable to add half-hitches only after all constructs have been placed, deployed, and tensioned as desired. Other than the optional half-hitches, no knots need to be tied during the course of the illustrated procedure.

Further, as also illustrated, the excess portions of either or both of the tails 630, 632 can be removed if desired. The stitch pattern resulting from the methods and shown in FIG. 12G is a mattress stitch pattern, but a person skilled in the art would be able to use other desired stitch patterns without departing from the spirit of the present disclosure. The resulting break strength of the formed stitch can be in the range of about 130 Newtons to about 225 Newtons without the formation of any half-hitches, and in one embodiment the break strength can be about 156 Newtons without the formation of any half-hitches. The use of half-hitches typically increases the load capacity.

Although in the illustrated embodiment the stationary terminal tail 632 is short, in other embodiments it can be longer for reasons described above and for other procedures. By way of non-limiting example, in one procedure, after the snare 646 and sliding knot 626 have been advanced to be adjacent to the tendon 1003, at least one half-hitch can be added to the stationary terminal tail 632 and then the remaining length of the tail 632 can be used for medial row fixation in a double row procedure such that two tails 630, 632 can be spanned over to medial row anchor(s). By way of further non-limiting example, a collapsing tail 630 can be spanned over to a lateral row anchor without locking the repair construct with an additional half-hitch. In this instance, however, the medial and lateral row fixations would not be independent of each other.

Further modifications to the method described with respect to FIGS. 12A-12G can include slidably coupling multiple repair constructs to the same anchor, which would provide the ability to incrementally and independently tension each construct with respect to the same anchor. Accordingly, a new repair technique can be implemented in which the tension on the whole repair construct can be tailored incrementally to eliminate undesired blemishes such as puckering and the formation of "dog-ears." Alternatively, multiple anchors, each having one or more repair constructs slidably coupled thereto, can be disposed at the surgical site and again incremental repair can be tailored for a more desirable result.

One exemplary embodiment of a method for performing a rotator cuff repair using the repair construct illustrated in FIGS. 9 and 11 is illustrated in FIGS. 13A-13D. A surgical opening can be formed through skin 1000 and a cannula can be passed therethrough to create a surgical repair site according to well known techniques. Similar to FIGS. 12A-12G, although cannulas are often used to define a channel through which the procedure can be preformed, the cannula is not shown in FIGS. 13A-13D for ease of illustration. Accordingly, to the extent the figures show components of the systems and devices passing through skin 1000, these components would typically be extending through the cannula, which itself is passed through the skin 1000.

As shown in FIG. 13A, the anchor 708 shown in FIG. 11 can be fixated into bone 1001 using ordinary techniques, such as by using a driver to screw or tap the anchor 708 into place. In the illustrated embodiment the suture shuttle 800, which includes the first end 802 having the snare 806 formed therein, is already coupled thereto, although in other embodiments the suture shuttle 800 can be slidingly coupled to the anchor 708 after the anchor 708 is positioned at its desired location.

Figure 13C:
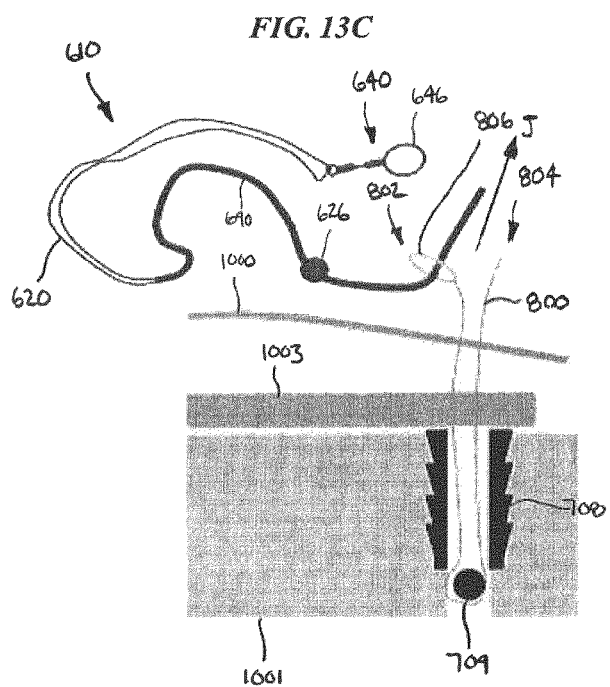
Figure 13D:
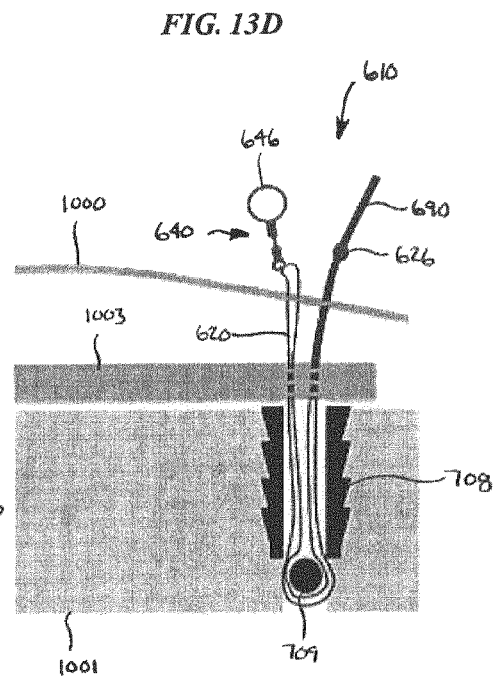

As shown in FIG. 13B, the first and second ends 802, 804 of the suture shuttle 800 can be passed through detached soft tissue, such as tendon 1003. As shown in FIG. 13C, a portion of the repair construct 610 of FIG. 9 can be passed through the snare 806. The snare 806 can then be collapsed, thereby coupling the repair construct 610 to the shuttle 800. Although the snare 806 is the mechanism used to couple the shuttle 800 and the construct 610, a variety of other coupling techniques can also be used to couple the repair construct 610 to the suture shuttle 800. A force approximately in the direction J can then be applied to the second end 804 to pull the first end 802, and thus the repair construct 610, through the tendon 1003 at a first location, around the filament engagement feature 709, and through the tendon 1003 at a second location. As a result, the snare linkage 640 can be disposed on one side of the anchor 708 and the sliding knot 626 can be disposed on the other side of the anchor 708, with the collapsible loop 620 being slidingly engaged with the filament engagement feature 709. The optional, removable sleeve 690 can be particularly useful in this embodiment because the knot 626 passes through the tendon 1003 twice, and also around the anchor 708, and thus the less friction and suture management capabilities it affords can be helpful. Further, once the shuttle 800 has moved the construct 610 to the desired location, the shuttle 800 can be de-coupled from the repair construct 610. Once the construct 610 is in place as illustrated in FIG. 13D, the construct 610 can be operated in a manner similar to as described with respect to FIGS. 12D-12G.

In some embodiments, the anchor 708 can include multiple suture shuttles coupled thereto to allow for multiple repair constructs that can be independently and sequentially deployed to be used in a surgical procedure. Alternatively, a surgeon can use a single shuttle to install multiple constructs on the same anchor, or still further, multiple anchors can be fixated for a procedure with each having its own repair construct or shuttle, or one suture shuttle can be used to place one or more constructs at multiple anchors.

Although in the illustrated embodiments the construct 610 is passed through two portions of tendon 1003, alternatively the construct 610 can be passed through only one portion of tendon or tissue while the second portion of the construct 610 can be free of the tendon or tissue. Either of the two ends can be the end that is not passed through the tendon or tissue, however, if a snare linkage 640 is not passed through tissue, a flexible member 670 to serve as a suture pin can be omitted and can be replaced, if desired, by any technique or mechanism used to prevent unintentional collapse of the snare 646, such as a spacer or tube. Still further, rather than passing through tissue, a repair construct can be coupled to tissue using other techniques, such as, for example, by wrapping the construct around the tissue.

Figure 14A:
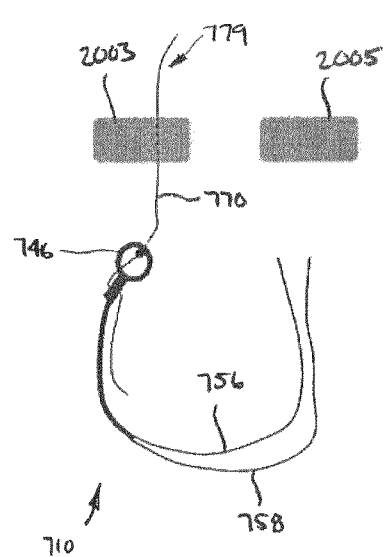
FIGS. 14A-14C are sequential views of one exemplary embodiment for using a surgical repair construct to draw two tissues closer together.
Figure 14B:
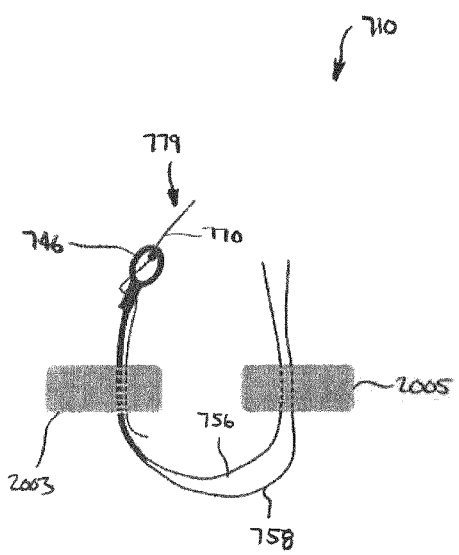
Figure 14C:
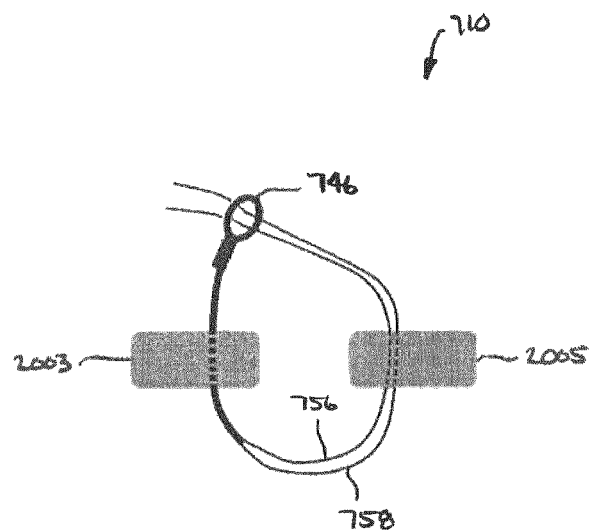

In an alternative embodiment, a repair construct can be used to pull two or more tissues into proximity with each other. Any of the repair constructs provided herein, or derivations thereof, can be used in conjunction with techniques of this nature. As shown in FIG. 14A, a repair construct 710 includes a collapsible snare 746 having a filament member 770 that is operable as both a suture pin and a suture shuttle, with two terminal limbs 756, 758 extending from a tubular portion 753. A terminal portion 779 of the flexible member 770 can be passed through a first tissue 2003, optionally using a needle or similar tool or device coupled to the terminal portion 779 to assist with threading the flexible member 770 through the first tissue 2003, to pull the snare 746 and a portion extending distally from the snare 746 through the first tissue 2003, as shown in FIG. 14B. As also shown in FIG. 14B, the terminal limbs 756, 758 can be passed through a second tissue 2005, also optionally using a needle or similar tool or device for each limb 756, 758 to assist with threading the limbs 756, 758 through the second tissue 2005. Once both the snare 746 and the two terminal limbs 756, 758 are on a superior side of the tissue 2003, 2005, at least a portion of the limbs 756, 758 can be passed through the snare 746, as shown in FIG. 14C, and then the snare 746 can be dressed to secure the two pieces of tissue 2003, 2005 together. The limbs 756, 758 can be subsequently tensioned to pull the two tissues 2003, 2005 closer together. Further, although the embodiment illustrated in FIGS. 14A-14C is directed to pulling together two tissues 2003, 2005, a person skilled in the art would be able to adapt these techniques for three or more tissues by passing the repair construct, or repair constructs, through additional tissue that is desired to be involved.

Other methods are provided herein that allow for objects, such as tissue, bone fragments, or a variety of other objects, to be fully secured using a single filament. One example is illustrated in FIGS. 15A-15G.

Figure 15A:
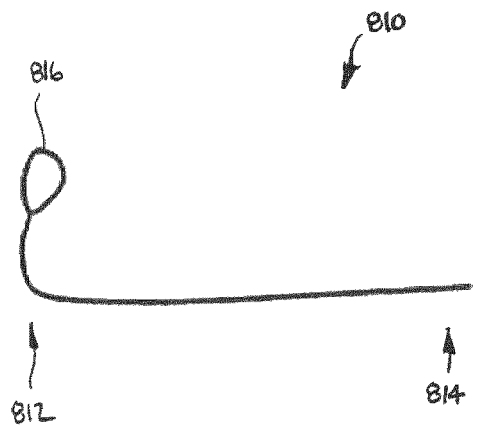

As shown in FIG. 15A, a flexible surgical filament 810 for use in a procedure can be provided, with the filament 810 including a first end 812 having a snare 816 formed therein and a second, leading end 814. The snare 816 can be formed in a variety of ways, including using techniques provided herein, as well as other known techniques. The leading end 814 can likewise have a variety of configurations, including having multiple limbs as provided in other embodiments of filament repair constructs disclosed herein, but as shown the leading end 814 is a single limb.

Figure 15B:
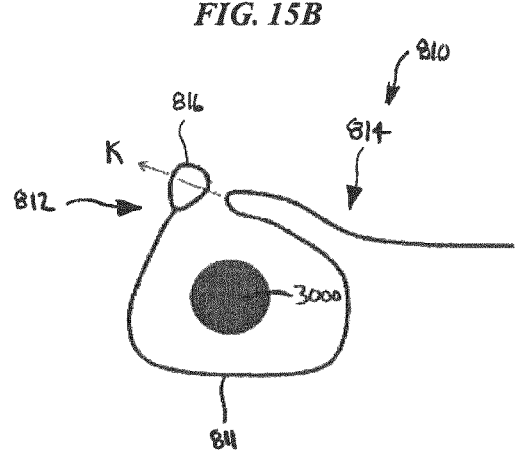

As shown in FIG. 15B, the filament 810 can be positioned substantially around an object 3000, such as tissue or bone fragments, to form a first loop 811, and the leading end 814 can be folded such that a portion thereof is substantially U-shaped. In other embodiments, the filament 810 can be preformed at the leading end 814 to have a substantially U-shaped configuration. The leading end 814 can be moved approximately in the direction K such that at least a portion of the substantially U-shaped leading end 814 passes through the snare 816, as shown in FIG. 15C. As a result, a portion of the leading end 814 remains on a first side of the snare 816 and a second loop 813 is formed by the portion of the filament that is within the snare 816, the second loop 813 being on the other side of the snare 816.

As shown in FIG. 15D, the snare 816 can be collapsed or dressed using techniques appropriate for the type of snare that is formed in the filament 810. Collapsing the snare 816 secures the first and second loops 811, 813, with the first loop 811 completely surrounding the object 3000 and the second loop 813 being adjacent to the object 3000. As shown in FIG. 15E, the first loop 811 can then be collapsed around the object 3000 such that the loop 811 engages and holds the object 3000. The first loop 811 can be collapsed, for example, by pushing the collapsed snare 816, which operates as a sliding knot, towards the object 3000 in the direction L.

The collapsed snare 816 can be pushed using a knot pushing device, by hand, or by other techniques and mechanisms for advancing collapsed snares and sliding knots. The collapsed snare 816 can be advanced in the direction L until no further tension can be provided and thus the filament of the first loop 811 is as fully engaged with the object 3000 as possible.

As shown in FIG. 15F, the leading end 814, starting with a terminal end 819 thereof, can be passed through the second loop 813. Once the leading end 814 is fully through the loop 813, tension can be applied to the leading end 814 in a direction M to collapse the second loop 813, as shown in FIG. 15G. The collapse of the second loop 813 results in a more secure hold of the object 3000 at least because it locks the previously collapsed snare 816 in place and provides additional load-bearing strength without adding half-hitches. The object 3000 is thus firmly and securely grasped by the filament 810 and can be moved and/or used as part of any number of surgical procedures.

FIGS. 16-22 illustrate a sampling of other procedures that can be performed in view of the systems and devices disclosed herein. To the extent these figures illustrate a snare, collapsible loop, filaments, and repair constructs, the various types of snares, loops, filaments, and repair constructs provided for herein can be used in conjunction with these procedures. Thus, the procedures illustrated are not limited to being preformed by only the systems and devices illustrated in FIGS. 16-22. Further, although in these embodiments the filaments are shows as being disposed in tissue, other techniques for associating tissue and filaments can be used, including wrapping the filaments around the tissue.

Figure 16:
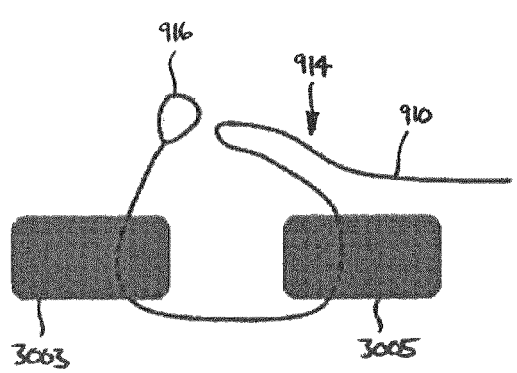
FIG. 16 is a schematic view of one exemplary embodiment of using a surgical filament to draw two tissues closer together.

FIG. 16 illustrates a filament 910 having a snare 916 and leading end 914 like the surgical filament 810 of FIGS. 15A-15G. As shown, the filament 910 is disposed through two separate tissues 3003, 3005, for instance by passing the leading end 914 through both tissues 3003, 3005, or by passing the snare 916 through one tissue 3003 and passing the leading end 914 through the other tissue 3005. The leading end 914 can then be folded into a substantially U-shaped configuration and the filament 910 can be operated in a manner similar to as described with respect to FIGS. 15A-15G. Thus, a second loop can be formed by collapsing the snare 916 around the leading end 914. The collapsed snare 916 can be advanced towards the tissue 3003, 3005 to draw the tissue 3003, 3005 closer together. Further, the second loop can be advanced distally by applying tension to the leading end 914, which can assist in maintaining the location of the collapsed snare 916, and thus the tissue 3003, 3005.

Figure 17:
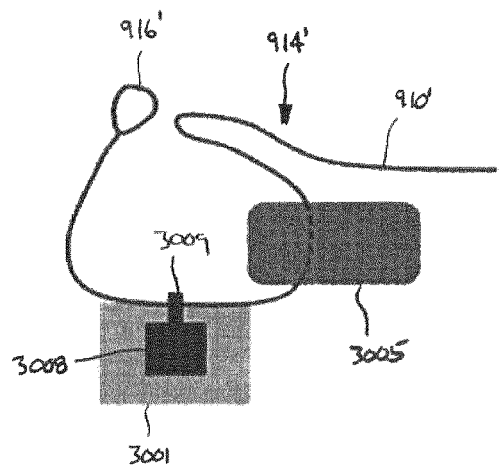
FIG. 17 is a schematic view of one exemplary embodiment of using a surgical filament to draw a tissue closer to bone.

FIG. 17 is similar to FIG. 16 except one of the tissues includes an anchor 3008 fixated in bone 3001. Thus, the filament 910' is passed through the tissue 3005 and through a connecting mechanism 3009 of the anchor 3008 in the bone 3001. The connecting mechanism 3009 can be any number of components used in bone anchors to allow suture to be coupled thereto, including but not limited to eyelets, posts, and other filament engagement features. Similar to the embodiment of FIG. 16, a second loop can be formed by collapsing the snare 916' around the leading end 914'. The collapsed snare 916' can be advanced distally to draw the tissue 3005 closer to the bone 3001. Further, the second loop can be advanced distally by applying tension to the leading end 914', which can assist in maintaining the location of the collapsed snare 916', and thus the tissue 3005 with respect to the bone 3001.

Figure 18:
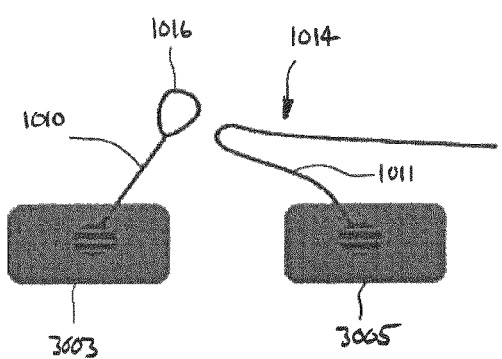
FIG. 18 is a schematic view of one exemplary embodiment of using two surgical filaments to draw two tissues closer together.
Figure 19:
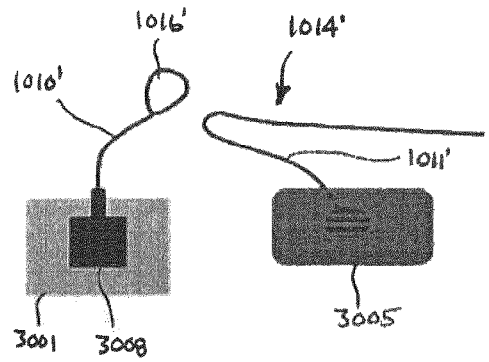
FIG. 19 is a schematic view of one exemplary embodiment of using two surgical filaments to draw a tissue closer to bone.

FIGS. 18 and 19 are similar to FIGS. 16 and 17, respectively, except rather than using a single filament 910, 910', two filaments 1010, 1010' and 1011, 1011' are used. One filament 1010, 1010' includes the snare 1016, 1016' and the second filament 1011, 1011' includes the portion 1014, 1014' previously described as a leading end. As shown, the first filament 1010, 1010' is associated with tissue 3003 (FIG. 18) or an anchor 3008 fixated in bone 3001 (FIG. 19) and a second filament 1011, 1011' is associated with tissue 3005 (FIGS. 18 and 19). The methods are then performed in a similar manner as described above with respect to FIGS. 16 and 17. Thus, a second loop can be formed by collapsing the snare 1016, 1016' around the second filament portion 1014, 1014'. The collapsed snare 1016, 1016' can be advanced distally to draw the tissue 3005 closer to tissue 3003 or the bone 3001. Further, the second loop can be advanced distally by applying tension to the portion 1014, 1014', which can assist in maintaining the location of the respective components 3001, 3003, 3005, and 3008 coupled to the filaments 1010, 1010' and 1011, 1011'.

Figure 20:
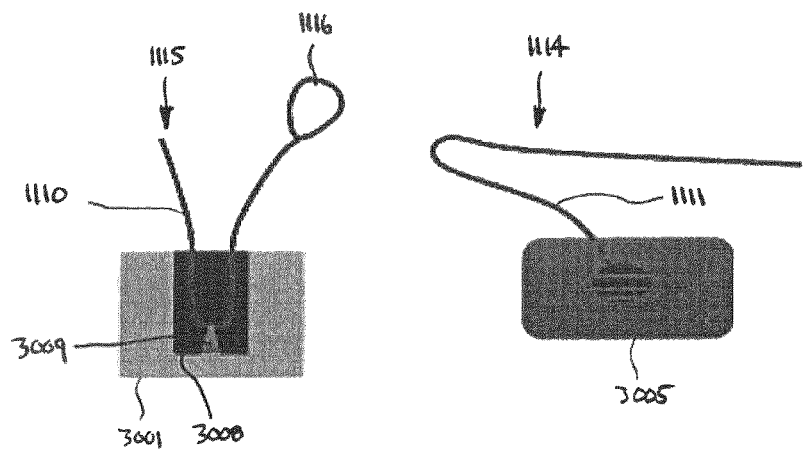
FIG. 20 is a schematic view of another exemplary embodiment of using two surgical filaments to draw a tissue closer to bone.

FIG. 20 illustrates another embodiment in which two filaments 1110, 1111 are used to draw tissue 3005 closer to an anchor 3008 disposed in bone 3001. The operation of this construct can be similar to those described above with respect to FIGS. 15A-19. As shown, a first filament 1110 having a snare 1116 and a terminal end 1115 is coupled to an anchor 3008 fixated in bone 3001. The anchor 3008 can include a one-way sliding mechanism 3009 to allow the terminal end 1115 to be used as a tensioning tail to collapse the snare 1116. The second filament 1111 can be coupled to the tissue 3005, the second filament 1111 having a leading end 1114 that can be folded to have a substantially U-shaped configuration. The leading end 1114 can be disposed in the snare 1116 and the snare can be collapsed to form a second loop. The collapsed snare 1116 can be advanced distally to draw the tissue 3005 towards the bone 3001, for instance by applying tension to the terminal end 1115. Further, the second loop can be advanced distally by applying tension to the leading end 1114, which can assist in maintaining the location of the tissue 3005 with respect to the bone 3001. Final tensioning can be carried out by applying tension to the terminal end 1115.

Figure 21:
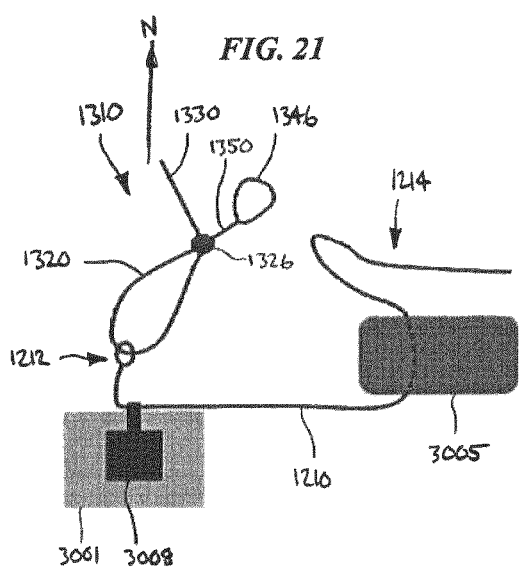
FIG. 21 is a schematic view of one exemplary embodiment of using a surgical repair construct and a filament to draw a tissue closer to bone.
Figure 22:
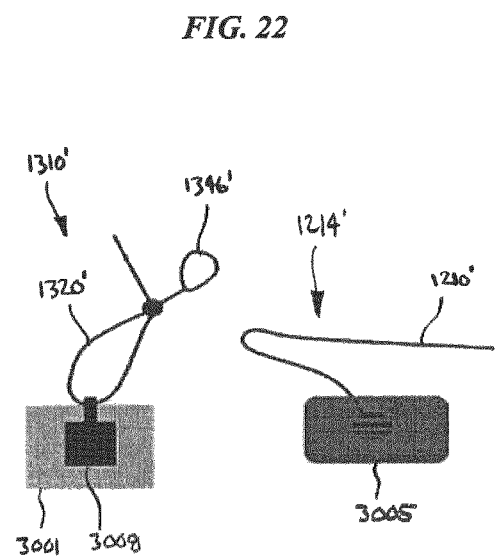
FIG. 22 is a schematic view of another exemplary embodiment of using a surgical repair construct and a filament to draw a tissue closer to bone.

FIGS. 21-22 illustrate yet two further embodiments of constructs for use for drawing tissue to bone, the operation of which can be similar to those described above with respect to FIGS. 15A-20. FIG. 21 includes a first filament 1210 having a first end 1212 configured to couple to a repair construct 1310 and a second leading end 1214, with the first end 1212 being coupled to an anchor 3008 disposed in bone 3001 and the second end 1214 being disposed through tissue 3005. A second filament forms a repair construct 1310 having a collapsible loop 1320, a snare 1346, and a connecting neck 1350 disposed therebetween. The loop 1320 includes a sliding knot 1326 and has a collapsible tail 1330 operable to collapse the loop 1320 by moving the knot 1326 distally toward the anchor 3008. Similar to other embodiments described herein, the collapsible tail 1330 can advance the sliding knot 1326 in a ratchet-like or incremental fashion. The leading end 1214 can be folded to have a substantially U-shaped portion, which can be passed through the snare 1346. The snare 1346 can be collapsed around the leading end 1214 to form a second loop. The sliding knot 1326 can be advanced distally, for instance by tensioning the tail 1330 in a direction N, thereby drawing the tissue 3005 toward the bone 3001. Further, the second loop can be advanced distally by applying tension to the leading end 1214, which can assist in maintaining the location of the sliding knot 1326, and thus the tissue 3005 with respect to the bone 3001. Final tensioning can be carried out by applying tension to the collapsible tail 1330.

The method illustrated in FIG. 22 is similarly operated as the method described with respect to FIG. 21, but the collapsible loop 1320' of the repair construct 1310' is coupled directly to the anchor 3008. Once a first filament 1210' is coupled to the repair construct 1310' by collapsing the snare 1346' around the leading end 1214' of the first filament 1210' disposed therein, collapsing the loop 1320' draws the tissue 3005 towards the bone 3001 in which the anchor is disposed.

The methods of FIGS. 21 and 22 could also be used in conjunction with multiple tissues and no anchors and bone, and any of the methods of FIGS. 16-22 can be used with any number of components being drawn together, such as anchors, bone, and tissue, including more than two components, as well as any number of filament construct combinations without departing from the spirit of the present disclosure.

One skilled in the art will appreciate further features and advantages of the invention based on the above-described embodiments. Accordingly, the invention is not to be limited by what has been particularly shown and described, except as indicated by the appended claims. Further, although the systems, devices, and methods provided for herein are generally directed to surgical techniques, at least some of the systems, devices, and methods can be used in applications outside of the surgical field. By way of non-limiting example, the methods of grasping objects described with respect to FIGS. 15A-15G can be used in contexts outside of surgical procedures and outside of the medical field. All publications and references cited herein are expressly incorporated herein by reference in their entirety.

What is claimed is:

1. A surgical method, comprising:
    selecting a flexible surgical filament having a snare at a first terminal end thereof and an opposed leading end disposed at a second opposed terminal end thereof;
    coupling the flexible surgical filament to an anchor disposed in bone such that the first terminal end and the second opposed terminal end are disposed on opposed lateral sides of the anchor;
    coupling the flexible surgical filament to tissue;
    passing a portion of the second opposed terminal end of the filament through the snare such that the leading end remains on one side of the snare, a first loop is formed that is coupled to both the anchor and the tissue, and a second loop is formed by the portion of the filament passed through the snare and is on another side of the snare;
    collapsing the snare around the filament disposed therein to secure the first loop and the second loop, the second loop being adjacent to at least one of the anchor or the tissue;
    collapsing the first loop to draw the tissue towards the anchor;
    passing the leading end of the filament through the second loop; and
    collapsing the second loop around the filament to secure a location of the tissue with respect to the anchor.

2. The method of claim 1, wherein collapsing the first loop further comprises pushing the collapsed snare towards the anchor.

3. The method of claim 1, wherein collapsing the second loop around the filament further comprises tensioning the leading end of the filament.

4. The method of claim 1, wherein the snare is defined by a sliding knot.

5. The method of claim 1, wherein passing a portion of the filament through the snare further comprises passing two portions of the filament through the snare such that two portions of the filament are disposed within the snare.

6. The method of claim 1, wherein passing a portion of the filament through the snare further comprises folding the filament into a U-shaped portion, and passing at least a portion of the U-shaped portion through the snare such that two portions of the filament are disposed within the snare.

7. A surgical method, comprising:
    selecting a flexible surgical filament having a snare at a first end thereof and an opposed leading end;
    coupling the surgical filament to a first object and a second object to form a first loop;
    passing a portion of the filament through the snare such that the leading end remains on one side of the snare without passing the leading end through the snare and a second loop formed by the portion of the filament passed through the snare is on another side of the snare;
    collapsing the snare around the filament disposed therein to secure the first loop and the second loop, the second loop being adjacent to at least one of the first object or the second object;

collapsing the first loop to draw the first object towards the second object;

passing the leading end of the filament through the second loop; and collapsing the second loop around the filament.

8. The method of claim 7, wherein collapsing the first loop further comprises pushing the collapsed snare towards at least one of the first object and the second object.

9. The method of claim 7, wherein collapsing the second loop around the filament further comprises tensioning the leading end of the filament.

10. The method of claim 7, wherein the snare is defined by a sliding knot.

11. The method of claim 7, wherein passing a portion of the filament through the snare further comprises passing two portions of the filament through the snare such that two portions of the filament are disposed within the snare.

12. The method of claim 11,
wherein the first object is a first tissue, and
wherein the second object is a second tissue.

13. The method of claim 7, wherein passing a portion of the filament through the snare further comprises folding the filament into a U-shaped portion, and passing at least a portion of the U-shaped portion through the snare such that two portions of the filament are disposed within the snare.

14. A surgical method, comprising:
selecting a first surgical filament having a snare and a second surgical filament having a leading end;
coupling the first surgical filament to a first object;
coupling the second surgical filament to a second object;
passing two portions of the second surgical filament through the snare to form a loop on one side of the snare with the leading end on another side of the snare, wherein the two portions of the second surgical filament form a U-shape;
collapsing the snare around the two portions of the second surgical filament disposed therein to secure the loop;
advancing the snare towards at least one of the first object or the second object to draw the first object towards the second object;
passing the leading end of the second surgical filament through the loop; and
collapsing the loop around the filament.

15. The method of claim 14,
wherein the first object is one of tissue and an anchor disposed in bone, and
wherein the second object is tissue, or a second tissue if the first object is tissue.

16. The method of claim 14, wherein collapsing the loop around the filament further comprises tensioning the leading end of the second surgical filament.

17. The method of claim 14, wherein the snare is defined by a sliding knot.

18. The method of claim 14, wherein the first surgical filament further comprises a repair construct having a collapsible loop, the snare, and a neck disposed between the collapsible loop and the snare.

19. The method of claim 18, further comprising collapsing the collapsible loop of the repair construct to draw the second object towards the first object.

20. A surgical method, comprising:
selecting a flexible surgical filament having a first snare at a first terminal end thereof and an opposed leading end disposed at a second opposed terminal end thereof, the first snare having coupled thereto a repair construct having a collapsible loop, a second snare, and a neck disposed between the collapsible loop and the second snare;
coupling the flexible surgical filament to an anchor disposed in bone such that the first terminal end and the second opposed terminal end are disposed on opposed lateral sides of the anchor;
coupling the flexible surgical filament to tissue;
passing a portion of the second opposed terminal end of the filament through the second snare such that the leading end remains on one side of the second snare, a first loop is formed that is coupled to both the anchor and the tissue, and a second loop is formed by the portion of the filament passed through the second snare and is on another side of the second snare;
collapsing the second snare around the filament disposed therein to secure the first loop and the second loop, the second loop being adjacent to at least one of the anchor or the tissue;
collapsing the first loop to draw the tissue towards the anchor;
passing the leading end of the filament through the second loop; and
collapsing the second loop around the filament to secure a location of the tissue with respect to the anchor.

21. The method of claim 20, wherein collapsing the first loop further comprises pushing the collapsed snare towards the anchor.

22. The method of claim 20, wherein collapsing the second loop around the filament further comprises tensioning the leading end of the filament.

23. The method of claim 20, wherein passing a portion of the filament through the second snare further comprises passing two portions of the filament through the second snare such that two portions of the filament are disposed within the second snare.

24. The method of claim 20, wherein passing a portion of the filament through the second snare further comprises folding the filament into a U-shaped portion, and passing at least a portion of the U-shaped portion through the second snare such that two portions of the filament are disposed within the second snare.

25. The method of claim 20, further comprising collapsing the collapsible loop to draw the tissue towards the anchor.

* * * * *